(12) United States Patent
Mitsudou et al.

(10) Patent No.: US 7,029,492 B1
(45) Date of Patent: Apr. 18, 2006

(54) IMPLANTING STENT AND DILATING DEVICE

(75) Inventors: Kazuaki Mitsudou, Okayama (JP); Yousuke Moriuchi, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/518,540

(22) Filed: Mar. 3, 2000

(30) Foreign Application Priority Data

Mar. 5, 1999 (JP) .................................. 11-058487

(51) Int. Cl.
*A61F 2/06* (2006.01)
(52) U.S. Cl. .................................................... 623/1.15
(58) Field of Classification Search ............... 623/1.15, 623/1.11–1.14, 1.16–1.17, 1.23, 1.36, 23.7, 623/900
See application file for complete search history.

(56) References Cited

U.S. PATENT DOCUMENTS

| 4,733,665 A | 3/1988 | Palmaz |
| 4,886,062 A | 12/1989 | Wiktor |
| 5,591,197 A * | 1/1997 | Orth et al. ................... 606/191 |
| 5,665,103 A * | 9/1997 | Lafontaine et al. ......... 606/192 |
| 5,697,971 A | 12/1997 | Fischell et al. |
| 5,876,449 A | 3/1999 | Starck et al. |
| 5,902,332 A | 5/1999 | Schatz |
| 6,027,527 A * | 2/2000 | Asano et al. ............... 623/1.15 |
| 6,183,506 B1 * | 2/2001 | Penn et al. ................. 623/1.15 |
| 6,231,598 B1 * | 5/2001 | Berry et al. ................ 623/1.15 |
| 6,299,635 B1 * | 10/2001 | Frantzen .................... 623/1.17 |

FOREIGN PATENT DOCUMENTS

| DE | 19728337 | * | 1/1999 |
| EP | 0 312 852 | | 4/1989 |
| EP | 0 364 787 | | 4/1990 |
| EP | 0 732 088 | | 9/1996 |
| EP | 0 734 698 | | 10/1996 |
| JP | 1-145076 | | 6/1989 |
| JP | 2-174859 | | 7/1990 |
| JP | 4-6377 | | 2/1992 |

* cited by examiner

Primary Examiner—(Jackie) Tan-Uyen T. Ho
(74) Attorney, Agent, or Firm—Buchanan Ingersoll PC

(57) ABSTRACT

A stent has a plurality of wavy annular members each formed of a narrow wavy element and arranged in the axial direction thereof; and a plurality of connection portions each connecting the adjacent wavy annular members to each other axially. The connection portion located in the vicinity of the axial center of the stent is weaker than other constituent parts of the stent and can be broken. That is, an inflating balloon catheter can be inserted into the stent such that the inflating balloon catheter penetrates through a side wall of the stent from its interior after the stent dilates radially. The connection portion can be broken by inflation of the balloon of the inflating balloon catheter.

11 Claims, 24 Drawing Sheets

US 7,029,492 B1

IMPLANTING STENT AND DILATING DEVICE

BACKGROUND OF THE INVENTION

The present invention relates to a stent that is implanted in lumens such as the blood vessel, the bile duct, the trachea, the esophagus, the ureter, and the like so that it is used to improve a stenosed portion or a dosed portion generated in the lumens.

To cure various diseases that are caused when the blood vessel or other lumens are stenosed or dosed, the stent which is a tubular-shaped medical appliance generally is implanted at the stenosed portion or the dosed portion to expand them and secure the lumen thereof.

Because the stent is inserted into the body from outside, its diameter is small. The stent is dilated to make its diameter large at the stenosed or dosed portions to keep the dilated state of the lumen.

The stent is classified into a self-expandable stent and a balloon expandable stent, depending on the function thereof and an implantation method. The balloon expandable stent which itself has no dilating function is secured at a desired portion. Then, a balloon provided in the stent is inflated to dilate (plastically deform) the stent so that the stent comes in dose contact with the inner surface of the desired lumen. That is, it is necessary to dilate the stent of this type in implanting it to the desired portion.

Balloon expandable stents are disclosed in Examined Japanese Patent Publication No. 4-6377 and Japanese Patent Application Laid-Open No. 2-174859. These stents are pipes having axial slots formed therein. The slots are arranged such that they may take inter-connected rhombus shapes when the stent is dilated.

The stent disclosed in Examined Japanese Patent Publication No. 4-6377 is superior in shape retention after dilation because slots take inter-connected rhombus shapes. That is, the stent is resistant to the contracting force of a blood vessel. In other words, the stent has a strong shape-holding force. Another advantage of the stent is that when increase in the diameter of the stent is desired in a dilated state, an additional balloon having an enlarged diameter may be inserted into the stent. The stent of this type is called tube type. The word tube type is derived from the fact that normally, the stent is manufactured by boring a hole on a metal tube (metal pipe) with a laser. The stent of this type has a structural characteristic that it consists of a large number of narrow members crossing each other.

In the stent disclosed in Examined Japanese Patent Publication No. 4-6377, supposing that one segment thereof consists of a long and narrow rectangle, one segment consists of long and narrow members crossing each other at six points. By dilating the long and narrow rectangle, the rectangle plastically deforms into a rhombic shape and maintains the deformed shape, thus being resistant to the contraction force of the blood vessel. The stent of the tube type has various shapes, in addition to the above configuration. But the stent of the tube type has a large number of cross points commonly, irrespective of configurations.

The stent disclosed in Japanese Patent Application Laid-Open No. 1-145076 is called coil-type stent consisting of one wire. The wire is deformed zigzag and wound spirally to form it into a cylindrical shape. Thus, the stent does not have any crossing points of wires.

When for example, the tube-type stent is implanted in a branched blood vessel, the long and narrow members are present at the branch portion, and the branch portion is always subjected to a blood stream. Thus, the tube-type stent may cause thrombus to arise at the branch portion. Another problem of the tube-type stent is that when the branch portion is stenosed again, it is impossible to expand the stenosed portion with a balloon or embed the stent therein, because the long and narrow member interferes with an operation.

On the other hand, the coil-type stent does not have crossing portions of wires. Therefore, it is possible to perform an operation of dilating the branch portion with the balloon. However, the coil-type stent does not have crossing portions of wires. Thus, it has a low force of keeping a dilated state. To increase the force of keeping a dilated state, it is necessary to thicken the wire. As a result, it is not easy to deliver the stent. Further, when the stent is caught by a blood vessel, the shape of the wire becomes out of order. That is, the coil-type stent is inferior to the tube-type stent in its function.

SUMMARY OF THE INVENTION

Therefore, it is an object of the present invention to provide a tube-type stent which is implanted in the body and capable of reducing the degree of inhibition of a blood stream to a branched blood vessel and capable of curing a stenosed portion of the branched blood vessel. It is another object of the present invention to provide a blood vessel dilation device having the stent. The object of this invention is to provide a stent that is to be implanted in a body formed in a substantially tubular configuration, has a diameter so set that the stent is inserted into the body, and can be dilated radially outwardly upon application of a force acting radially outwardly from the interior thereof, the stent having a plurality of wavy annular members each formed of a wavy element and arranged in the axial direction thereof; and a plurality of connection portions each connecting the adjacent wavy annular members to each other axially, wherein the connection portion is weaker than other parts and can be broken.

The object of this invention is to provide a dilation device having a tubular shaft body; a foldable and expandable balloon provided to a front-end portion of the shaft body; and a stent installed on the folded balloon and dilating by expansion of the balloon, wherein the stent is the above mentioned stent; the shaft body has a balloon expansion lumen communicating with the inside of the balloon; and the dilation device has a radiographing member fixed to an outer surface of the shaft body such that a fixing position of the radiographing member is located at a center of the stent or has two radiographing members fixed to the outer surface of the shaft body such that the fixing positions of the radiographing members are located at one and other ends of a central region, of the stent, having a predetermined length.

DETAILED DESCRIPTION OF THE PREFERRED EMBODIMENTS

An embodiment of the stent of the present invention will be described below with reference to the drawings.

A stent 1 of the present invention is a so-called balloon expandable stent. That is, the stent 1 is formed in a substantially tubular configuration and has a diameter so set that the stent 1 is inserted into the body. The stent 1 can be dilated radially outwardly upon application of a force acting radially outwardly from the interior of the tubular stent.

The stent 1 has a plurality of wavy annular members (wavy line-shaped annular member) 2a, 2b each formed of a narrow wavy element and arranged in the axial direction thereof; and a plurality of connection portions 4 each connecting the adjacent wavy annular members 2a, 2b to each other axially. The connection portion 4 located in the vicinity of the axial center of the stent 1 is weaker than the other constituent parts and can be broken. Owing to the construction, an inflating balloon catheter can be inserted into the stent 1 such that the inflating balloon catheter penetrates through a side wall of the stent from its interior after the stent is dilated radially. The connection portion 4 can be broken by the inflation of the balloon of the inflating balloon catheter.

Figure 1:
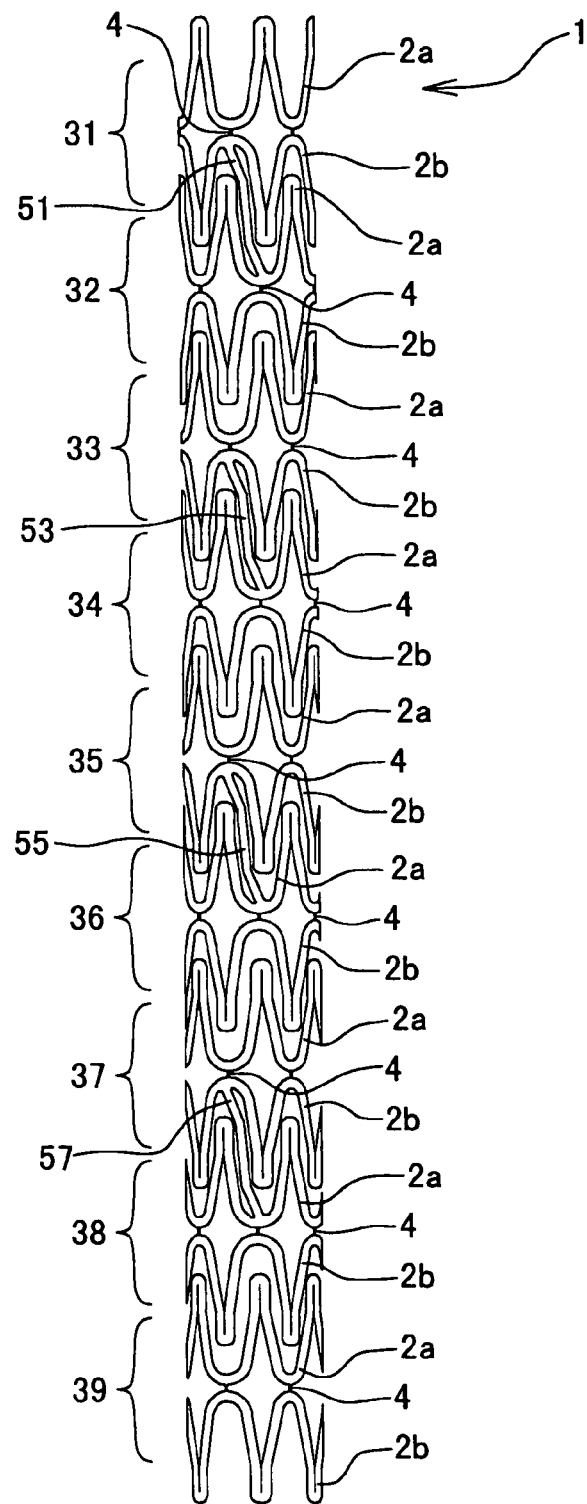
FIG. 1 is a front view of a stent according to an embodiment of the present invention.
Figure 2:
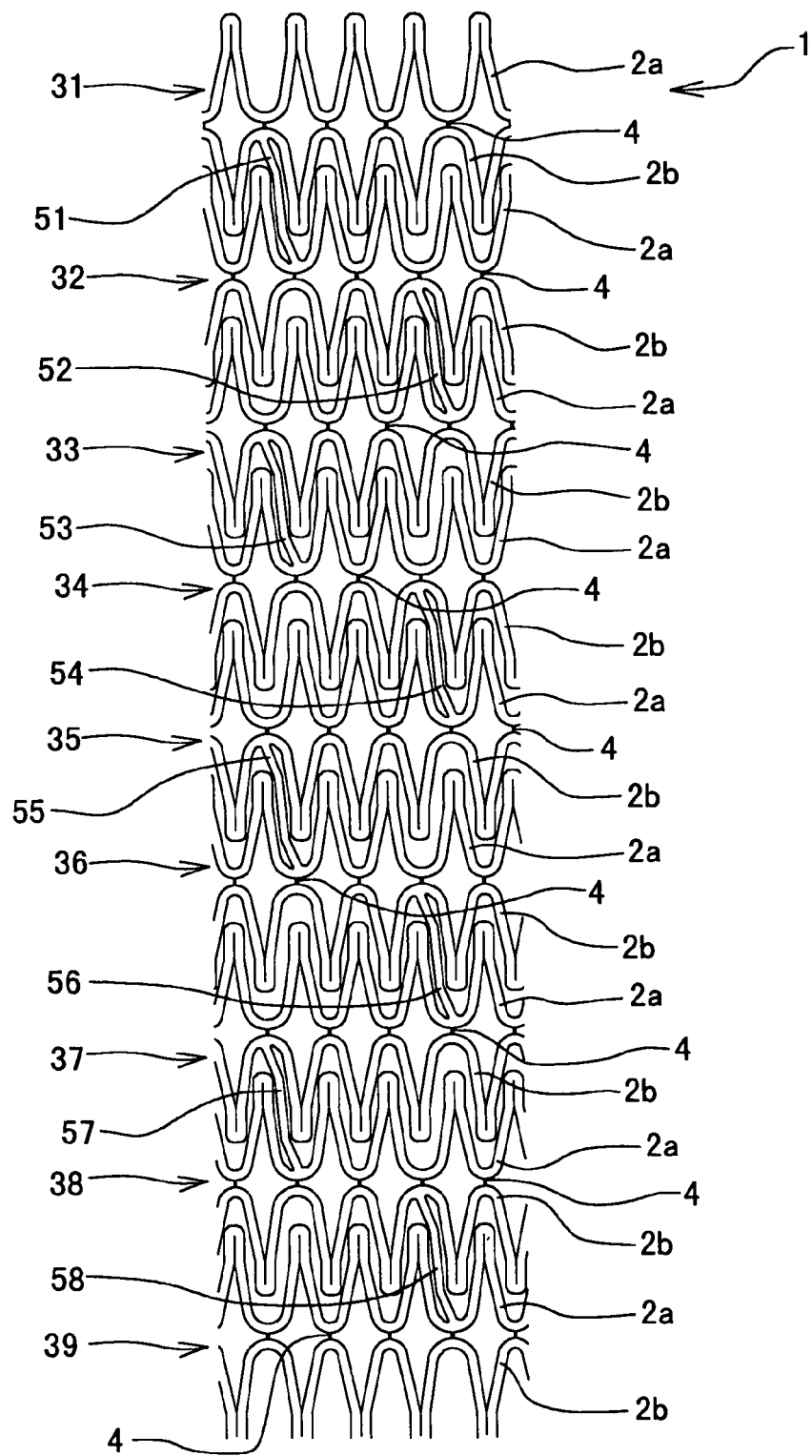
FIG. 2 is a development view of the stent of FIG. 1.
Figure 3:
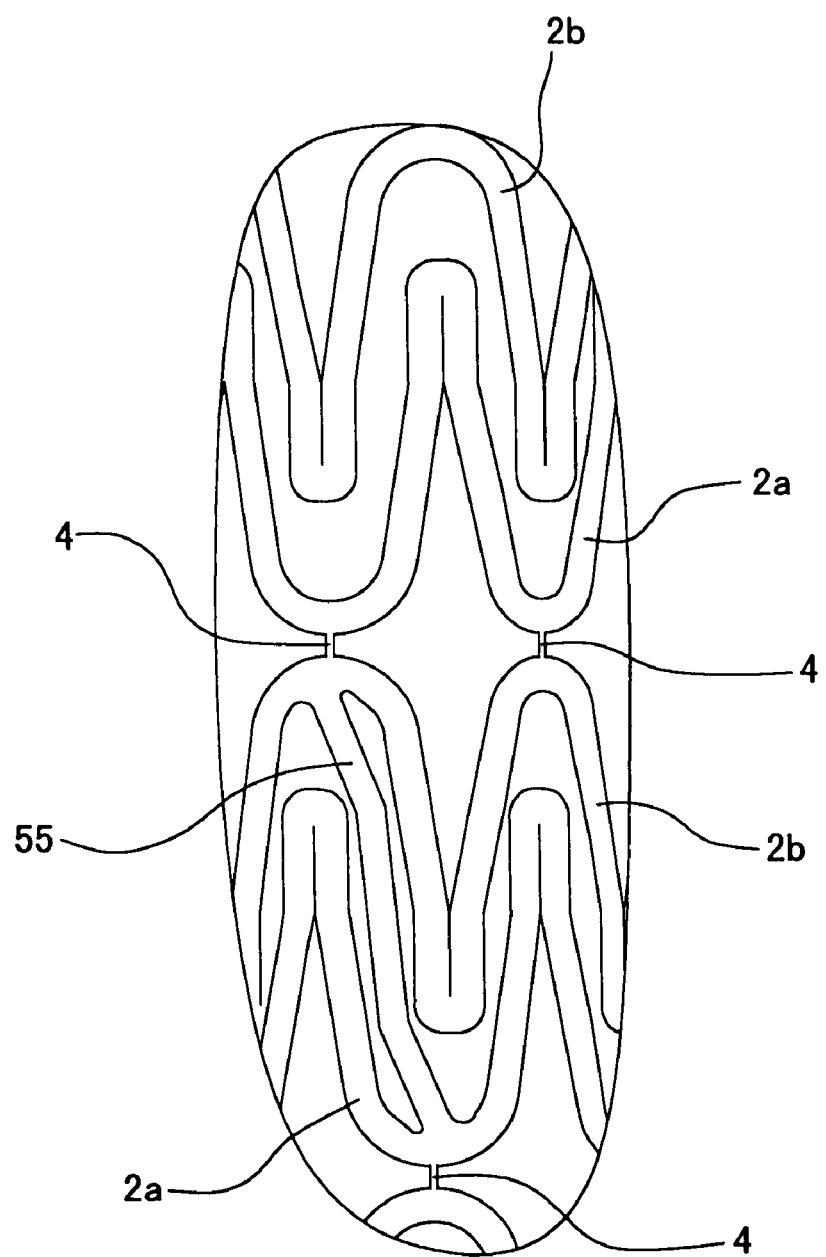
FIG. 3 is a partly enlarged front view of the stent of FIG. 1.

Specifically, as shown in FIGS. 1 through 3, the stent 1 comprises a plurality of annular units 31, 32, 33, 34, 35, 36, 37, 38, and 39 and joining portions 51, 52, 53, 54, 55, 56, 57, and 58. The annular units 31, 32, 33, 34, 35, 36, 37, 38, and 39 each has the first wavy annular member 2a formed of a narrow wavy element (preferably, having no edge); the second wavy annular member 2b disposed in the axial direction of the stent 1 such that a mountain of the second wavy annular member 2b is proximate to a valley of the first wavy annular member 2a and formed of a narrow wavy element (preferably, having no edge); and a plurality of narrow connection portions 4 (preferably, having no edge) each connecting the valley of the first wavy annular member 2a and the mountain of the second wavy annular member 2b to each other. A plurality of annular units is arranged approximately linearly in the axial direction of the stent 1. Each of the annular units has one of narrow joining portions 51, 52, 53, 54, 55, 56, 57, and 58 (preferably, having no edge) each connecting the wavy elements of the adjacent annular units to each other. The connection portion 4 located in the vicinity of the axial center of the stent 1 is weaker than the other constituent parts and can be broken. In other words, the stent 1 is a tubular body comprising a large number of annular units connected to each other with the connection portions.

As shown in FIGS. 1 and 2 which is a developed view of FIG. 1, each of the annular members 2a, 2b has five mountains and valleys spaced at almost the same intervals. Each of the annular members 2a, 2b is formed of a plurality of the wavy elements having no edge so that the wavy elements continue to become annular. It is preferable that the number of the mountains (valleys) of the annular member is four to seven. The second wavy annular member 2b is disposed in the axial direction of the stent 1 such that the mountain thereof is proximate to the valley of the first wavy annular member 2a. The valley of the first wavy annular member 2a and the mountain of the second wavy annular member 2b are connected to each other with a plurality of the short connection portions 4 to form one annular unit. In the embodiment, all the valleys of the first wavy annular member 2a and all the mountains of the second wavy annular member 2b are connected to each other with the connection portions 4. One annular unit has five (number of mountains or valleys of annular member) connection portions 4.

The stent 1 comprises the annular units 31, 32, 33, 34, 35, 36, 37, 38, and 39 (nine in the embodiment) constructed as described above and arranged in the axial direction of the stent 1 and a joining portion, respectively to connect the wavy annular members of the adjacent annular units to thereby form the cylindrical stent. Only one joining portion is formed between the adjacent annular units. The joining portions 51, 52, 53, 54, 55, 56, 57, and 58 are so disposed that the adjacent ones are not continuous with each other. The inside of the mountain of the wavy annular member 2b located at the start point of the joining portion (for example, 51) is formed wider than the other mountains thereof.

The connection portion 4 located in the vicinity of the axial center of the stent 1 is weaker than other constituent parts of the stent 1 and can be broken. As shown in FIGS. 1 through 3, in the stent 1 of the embodiment, the sectional area of each connection portion 4 has a smaller (in other words, narrower) sectional area than that of each of the other parts of the stent 1, namely, the wavy annular members 2a, 2b and the joining portions 51, 52, 53, 54, 55, 56, 57, and 58. That is, the connection portion 4 is weaker than the other parts of the stent 1. In particular, in the embodiment, the thickness of the connection portion 4 is almost equal to that of the other parts but the width thereof is smaller than that of the other parts.

The annular members 2a, 2b are formed not weakly but the connection portion 4 is formed weakly. A weak portion is not formed on the annular members 2a, 2b. If the weak portion is formed on the annular members 2a, 2b, the annular members 2a, 2b may be naturally broken when the stent 1 is dilated. That is, if the annular members 2a, 2b have the weak portion formed thereon, they may have a low dilating force. But even though the connection portion 4 is formed weakly, the connection portion 4 hardly deforms when the stent 1 is dilated. Thus, the connection portion 4 is hardly broken naturally when the stent 1 is dilated.

Figure 7:
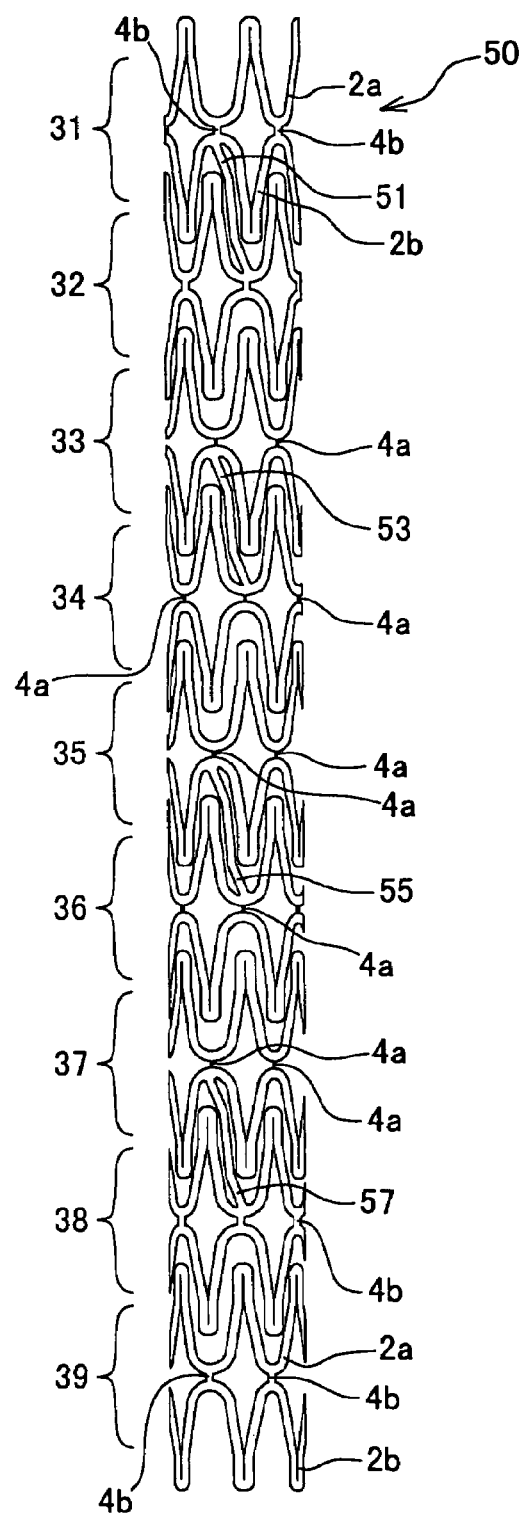
FIG. 7 is a front view of a stent according to another embodiment of the present invention.

Although all the connection portions 4 are weak in the embodiment, it is possible to form a weak connection portion 4a only in the vicinity of the axial center of the stent 50, as shown in FIG. 7 showing another embodiment. The length of the region in which the weak connection portion is formed is preferably 30–60% of the entire length of the stent 50. The region in which the weak connection portion is formed is so formed that the center thereof is located at approximately the center of the stent in the axial direction thereof. In the embodiment shown in FIG. 7, the connection portion 4b located in the vicinity of each axial end of the stent has a width equal to that of the wavy element of each of the annular members 2a, 2b and does not have the weak portion.

Further, instead of making the entire connection portions 4 weak but as shown in FIGS. 8 through 12 showing another embodiment, it is possible to form a weak portion on the connection portions 4 such that a portion having a smaller sectional area than the other constituent parts of the stent is formed on the connection portions 4 having the same sectional area as those of the other component parts. As the mode of the weak portion, for example, a nick is formed on each of the opposite side surfaces of the connection portion such that the nicks are axially spaced at a certain interval. As another example, one nick is formed on one side surface of the connection portion such that the nick extends to the widthwise center thereof. As still another example, two nicks are formed on both side surfaces of the connection portion such that the nicks extend to the widthwise center thereof and confront each other. As further example, a portion is formed on the connection portion such that the portion is shorter or thinner than other portions thereof. As still further example, a portion is formed on the connection portion such that the portion is shorter and thinner than other portions thereof.

Figure 4:
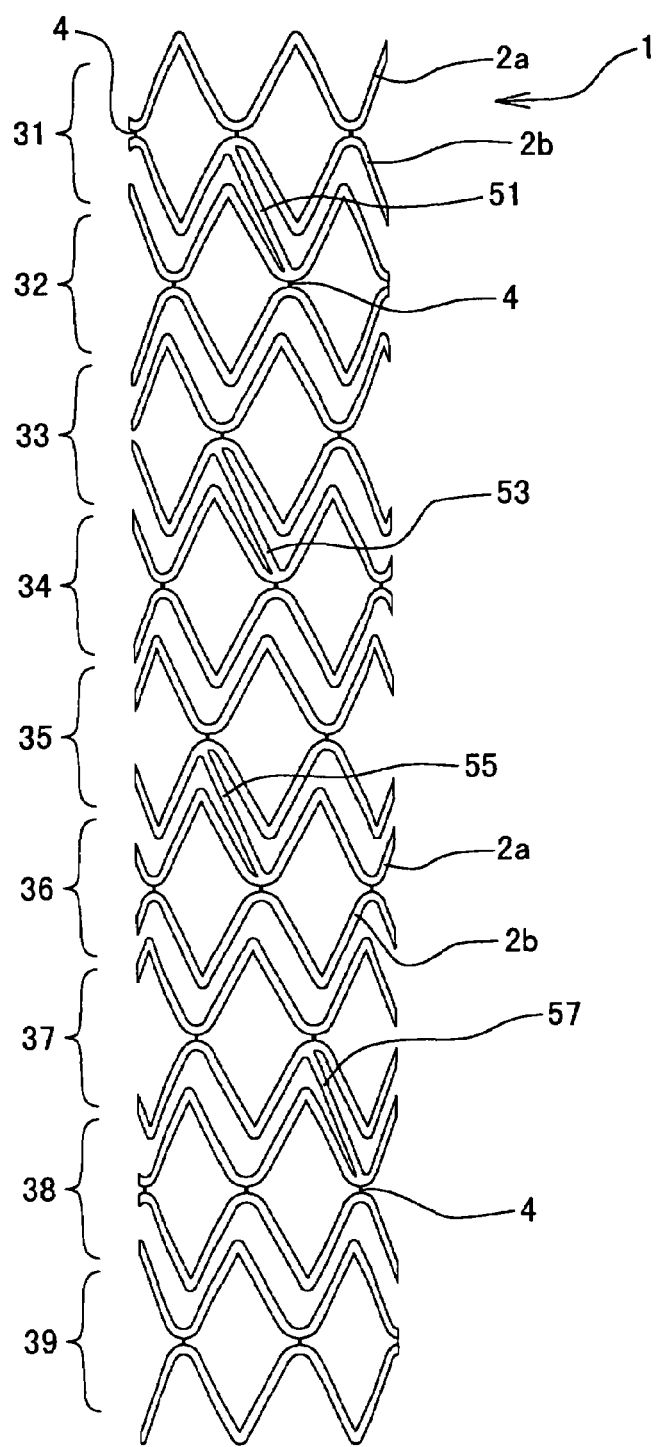
FIG. 4 is a front view of the dilated stent of FIG. 1.
Figure 19:
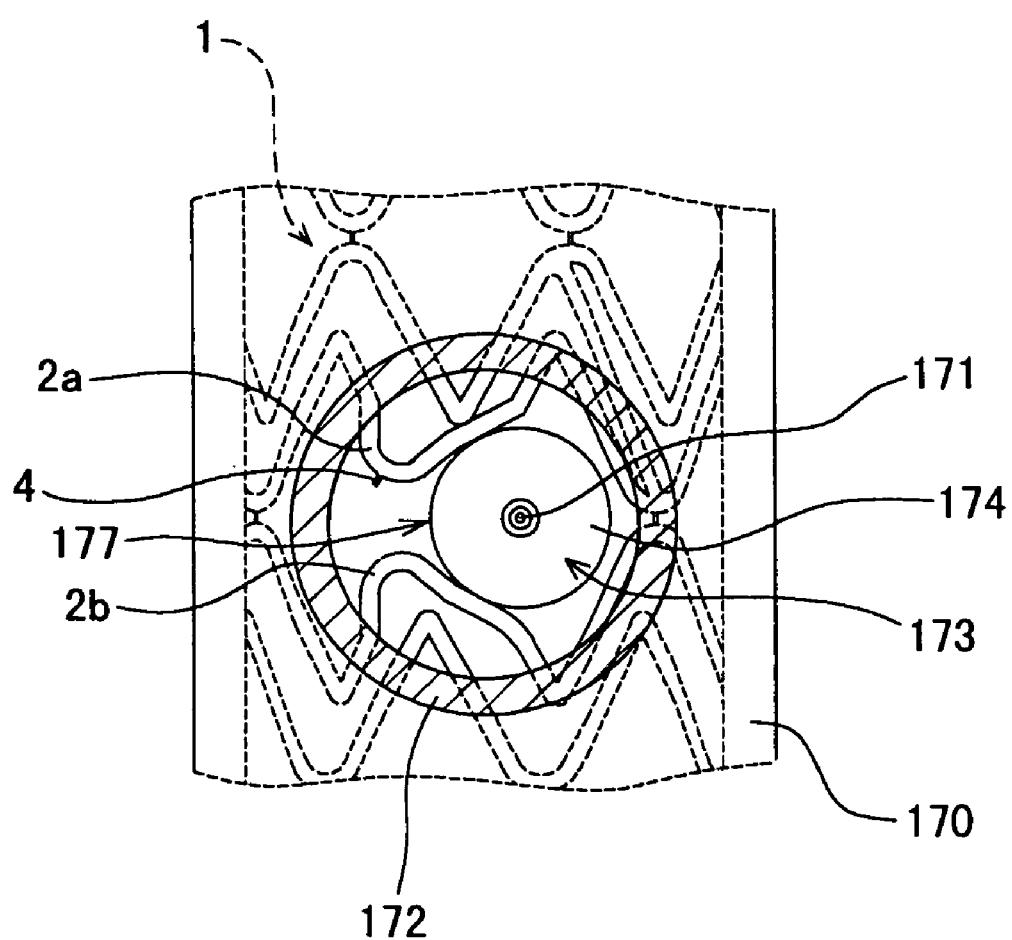
FIG. 19 is an explanatory view for describing the operation of the stent of the present invention.

An inflating balloon catheter can be inserted into each of the stents 1, 50 such that the inflating balloon catheter penetrates through a side wall of the stent from its interior after the stent is dilated radially. The connection portion can be broken by the inflation of the balloon of the inflating balloon catheter, as shown in FIG. 19. As shown in FIG. 4, each annular member keeps a dilated configuration. Thus the entire stent 1 also keeps a dilated configuration. When the inflating balloon catheter is inserted into the dilated stent and passed the side wall of the stent 1 by guiding with a guide wire and the balloon is inflated, the connection portion of the stent is cut off by the inflated balloon. As a result, a hole having a diameter almost equal to an enlarged diameter of the inflated balloon is formed through the side wall. If the stent does not have the weak connection portion, the inflating balloon catheter cannot secure a hole (space) larger than the space formed of a deformation of the annular members to the maximum. Thus, if the balloon is inflated forcibly, it bursts. That is, because the stent has the weak connection portion, the stent is stable in its configuration in a blood vessel.

The joining portions 51–58 joining the wavy annular members of the adjacent annular units 31–39 remain unchanged substantially in their lengths when the stent 1 is dilated. Because the joining portions 51–58 and the connection portion 4 remain substantially unchanged in their lengths even when the stent 1 is dilated, the overall length of the stent 1 remains substantially unchanged before and after dilation. It never happens that the stent is reduced in length after dilation.

Figure 5:
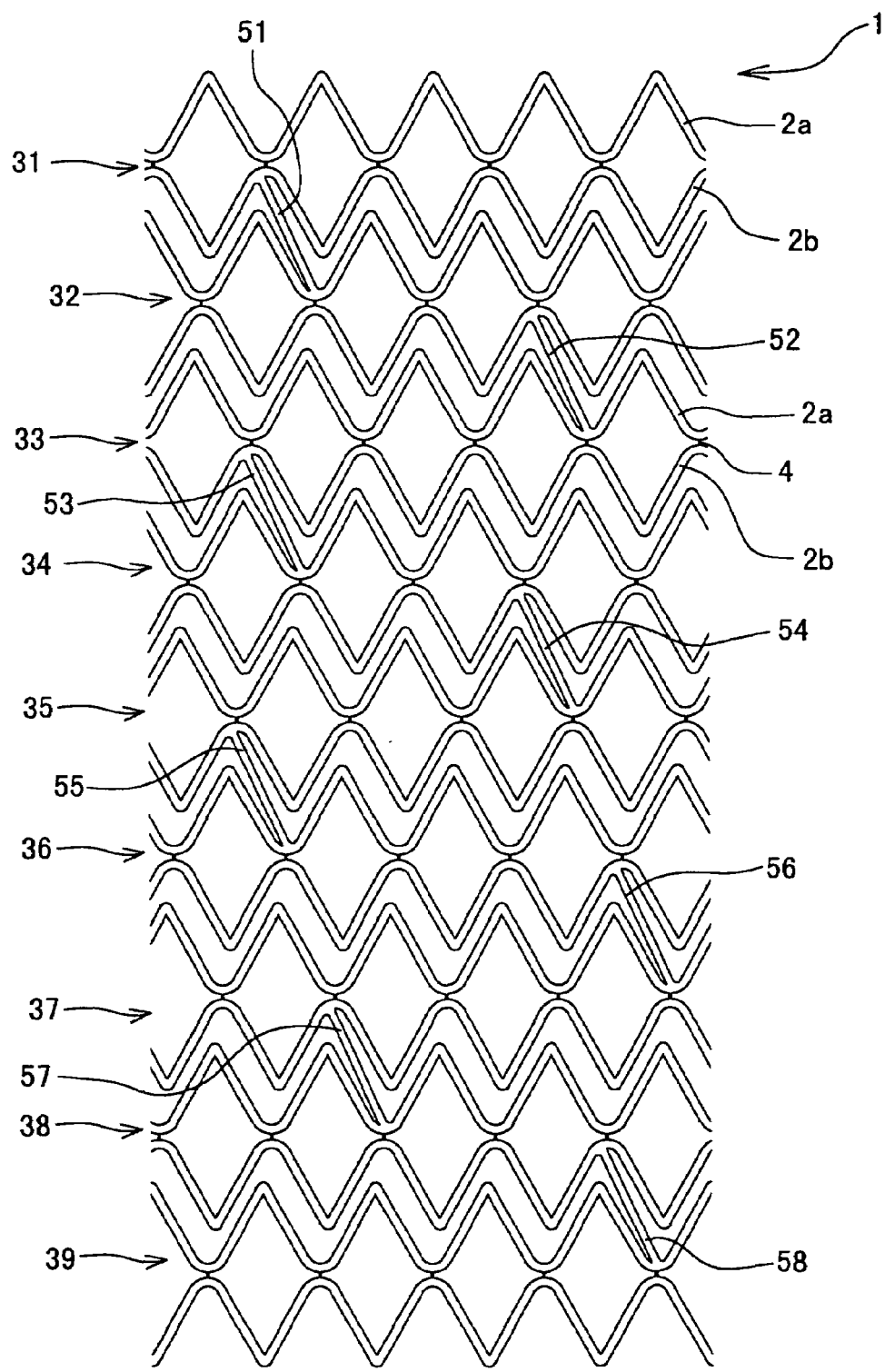
FIG. 5 is a development view of the dilated stent of FIG. 4.
Figure 6:
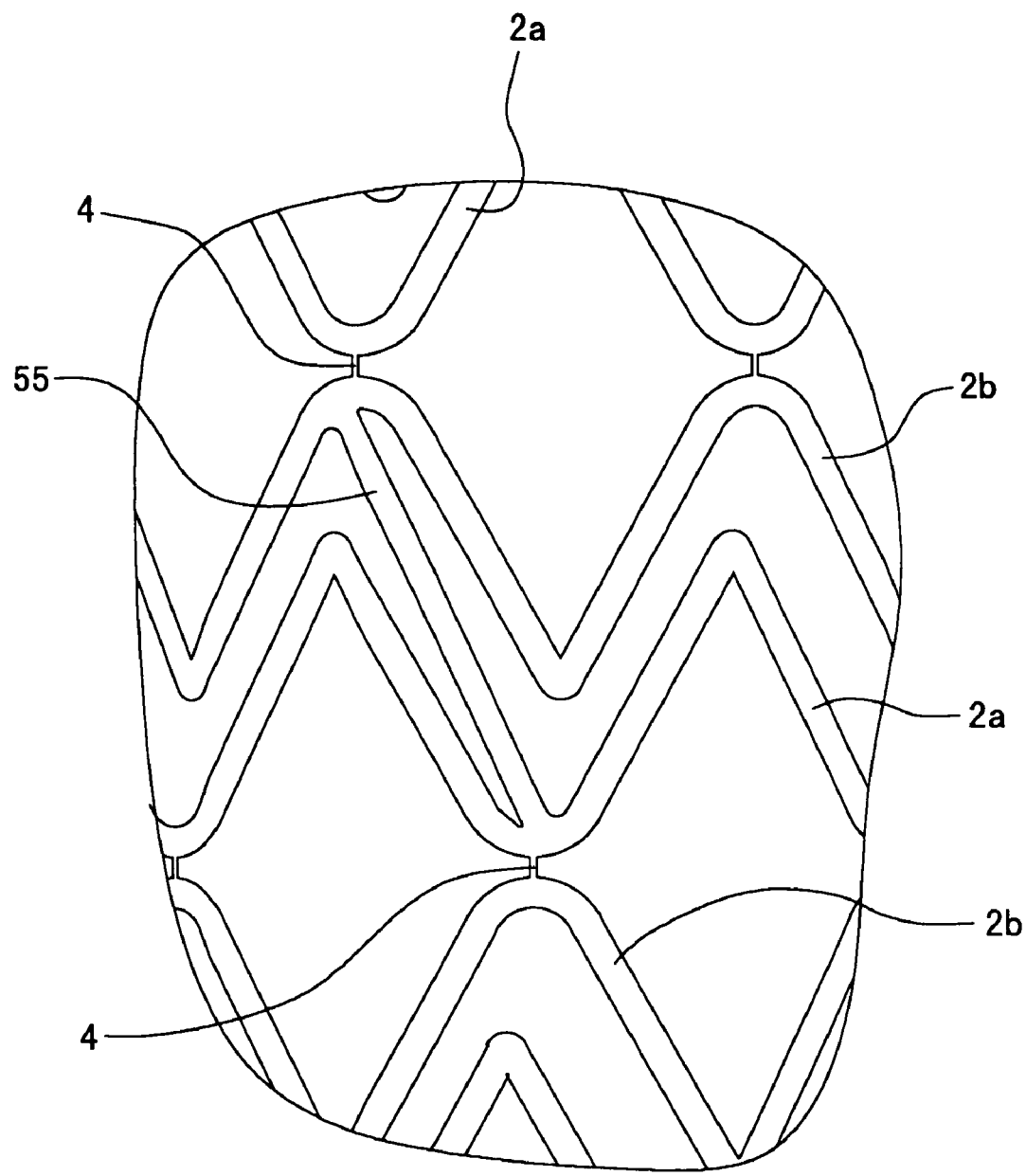
FIG. 6 is a partly enlarged front view of the dilated stent of FIG. 4.

The joining portion 51–58 is so disposed that it connects the adjacent annular units 31–39 at only one position. Although the adjacent annular units 31–39 may be connected at two or more positions, it is preferable to connect them at only one position as embodied in the present invention so that the stent follows deformation of a blood vessel faithfully. Further in the embodiment, the joining portion 51–58 is so disposed that the adjacent ones are not continuous with each other. Therefore, it is possible to prevent a load generated by one annular unit that has followed the deformation of a blood vessel from being directly (or linearly) transmitted to the unadjacent annular units. Thus it is possible to allow the respective annular units to independently display their dilation function. Further, as in FIGS. 2 and 5 showing one embodiment of the present invention, the joining portions 51–58 are so arranged that the odd joining portion and the even joining portion form 180 degrees therebetween at the axis of the stent. This construction is preferable because potential interactions between unadjacent annular units can be minimized.

To reduce the degree of damage to be applied to the inflated balloon when the connection portion 4 is broken, it is preferable that the edge of the wavy element of the stent is chamfered. As the method of chamfering the stent, after the stent is fabricated into a final shape, chemical polishing, electropolishing or mechanical polishing can be used. The chemical polishing is preferably carried out by dipping the stent in a chemical polishing solution for stainless steel. Any chemical polishing solution containing one capable of dissolving stainless steel may be used. For example, one preferable chemical polishing solution contains a mixture of hydrochloric acid and nitric acid serving as a base component and additives such as an organic sulfur compound for adjusting a dissolution rate, smoothing, and imparting luster and a surface active agent.

It is possible that the wavy element of the annular members 2a, 2b located at the opposed ends of the stent 1 in the axial direction thereof has a sectional area, respectively smaller than that of the other wavy annular members. This construction causes the dilation force of the wavy annular members located at the opposed ends of the stent 1 in the axial direction thereof to be lower than those of the other wavy annular members when the stent 1 dilates, but allows the annular members 2a, 2b located at the opposed ends of the stent 1 in the axial direction thereof to follow the bending of a blood vessel to a high extent. That is, the opposed ends of the stent 1 in the axial direction thereof have a high degree of affinity for the blood vessel. As the method of reducing the thickness of the annular members 2a, 2b located at the opposed ends of the stent 1 in the axial direction thereof, after the stent is fabricated into the final shape, the annular members 2a, 2b is chemically polished or mechanically polished.

It is possible that the material of the annular unit (annular member) located at the axial center of the stent 1 have the maximum cross-sectional area and that the annular units (annular member) located nearer to the axial end of the stent have a smaller cross-sectional area than the annular units located nearer to the center of the stent. Specifically, the thickness of the annular units are so set that the thickness of the annular units 34, 35, and 36 located at the axial central part of the stent 1 have a largest thickness and the other annular units have small thicknesses decreasingly as they are nearer to both axial ends of the stent. This construction ensures that the stent 1 displays a sufficient dilating force at its central part and faithfully follows a bent portion of a blood vessel. That is, both axial ends of stent 1 have better affinity for the blood vessel. It is also possible that the annular unit located at the center of the stent 1 has a maximum width and the other annular units have small widths decreasingly as they are nearer to both axial ends of the stent.

In the stent 1, a part of the wavy annular member 2a of one annular unit is in penetration into the wavy space formed at the axial end (inner side of stent) of the other annular unit adjacent to the one annular unit. That is, a part of the mountain of the wavy annular member 2a of one annular unit is in penetration into the concave portion of the wavy annular member 2b formed in the vicinity of the connection portion of the other annular unit adjacent to the one annular unit. Therefore, the adjacent annular units overlap partially each other when the stent 1 is viewed in the axial direction thereof. Thus, when the constituent elements of the wavy annular members are reduced in their lengths in the axial direction of the stent upon dilation of the stent, gaps on the side surface of the stent increase to a small extent. Therefore, it is possible to dilate a stenosed portion of a blood vessel securely and holds an affected portion without a gap.

The mountain of the annular member 2b having one of the joining portions 51, 52, 53, 54, 55, 56, 57, and 58 formed therein is wider than the other mountains thereof, such that a part of the mountain is adjacent to the joining portion. Similarly, the valley of the annular member 2a having one of the joining portions 51, 52, 53, 54, 55, 56, 57, and 58 formed therein is wider than the other valleys thereof, such that a part of the valley is adjacent to the joining portion. In the embodiment, the joining portion is curved. The curved joining portions 51, 52, 53, 54, 55, 56, 57, and 58 become approximately straight when the stent is dilated, as shown in FIGS. 4 and 5.

It is preferable that the material of the stent 1 has a certain degree of compatibility with an organism. For example, it is possible to use stainless steel, tantalum or tantalum alloys, platinum or platinum alloys, gold or gold alloys, cobalt base alloys and the like. It is preferable to plate the stent with a noble metal such as gold and platinum after the stent is fabricated into a final shape. As the stainless steel, SUS 316L most corrosion-resistant of the above metals can be preferably used.

It is preferable to anneal the stent 1 after it is fabricated into the final shape. Annealing improves the flexibility and plasticity of the entire stent so that the stent can be effectively implanted in a curved blood vessel. As compared with a non-annealed stent, the annealed stent has a lower force of restoring to an original state after it is dilated, and especially has a lower force of restoring to an original linear state when it is dilated at a curved portion of a blood vessel. This minimizes physical stimulation to the inner wall of the curved blood vessel, thus reducing the cause of a recurrence of stenosis. The stent is preferably annealed by heating it to 900 to 1200° C. in an inert gas atmosphere (e.g., a mixture gas of nitrogen and hydrogen) so that no oxide film is formed on the surface of the stent and then slowly cooling it.

The stent 1 has a diameter favorably 0.8 to 1.8 mm and more favorably 1.0 to 1.6 mm in an undilated state. The stent 1 has a length favorably 9 to 40 mm in an undilated state. The length of each of the wavy annular members 2a, 2b has a length of 0.7 to 2.0 mm. The length of one of the annular units 31 through 39 is favorably 1.5–4.0 mm and more favorably 2.0–3.0 mm. The length of one connection portion 4 is favorably 0.01–0.5 mm. The number of the annular units is 3 to 50. The constituent elements (annular member) of the adjacent annular units have an axial overlap of about 0.5 to 1 mm. The distance between the center of one annular units and that of the annular unit adjacent thereto is preferably 1.3 to 2.5 mm. The length of each of the joining portions 51, 52, 53, 54, 55, 56, 57, and 58 is preferably 1.4 to 2.7 mm. The angle of inclination (the angle of inclination of the joining portion relative to a longitudinal direction in a development view) of each of the joining portion 51 through 58 relative to the axis of the stent is favorably 0° to 30° and more favorably 5° to 25°.

The thickness of each of the wavy annular members 2a, 2b of the stent 1 and that of each of the joining portions 51, 52, 53, 54, 55, 56, 57, and 58 are favorably 0.05 to 0.15 mm and more favorably 0.08 to 0.12 mm. The width of each of the wavy annular members 2a, 2b and that of each of the joining portions 51, 52, 53, 54, 55, 56, 57, and 58 are favorably 0.07 to 0.15 mm and more favorably 0.08 to 0.12 mm. The thickness of the connection portion 4 of the stent 1 is favorably 0.05–0.12 mm and more favorably 0.06–0.10 mm. The width of the connection portion 4 of the stent 1 is favorably 0.01–0.05 mm and more favorably 0.02 to 0.04 mm. The sectional area of the connection portion 4 is favorably $1/50$ to $1/2$ of that of the other parts (annular member and joining portion) and more favorably $1/20$ to $1/10$ of that of the other parts.

Another embodiment of the stent of the present invention is described below.

Figure 8:
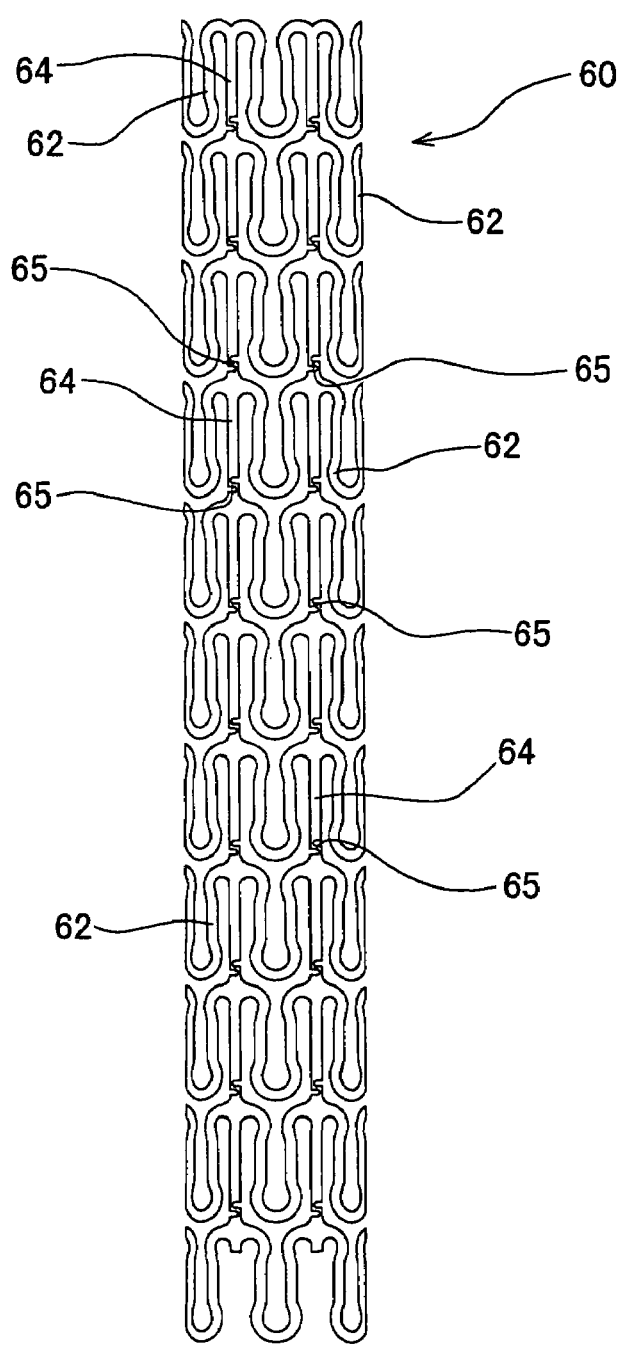
FIG. 8 is a front view of a stent according to still another embodiment of the present invention.
Figure 9:
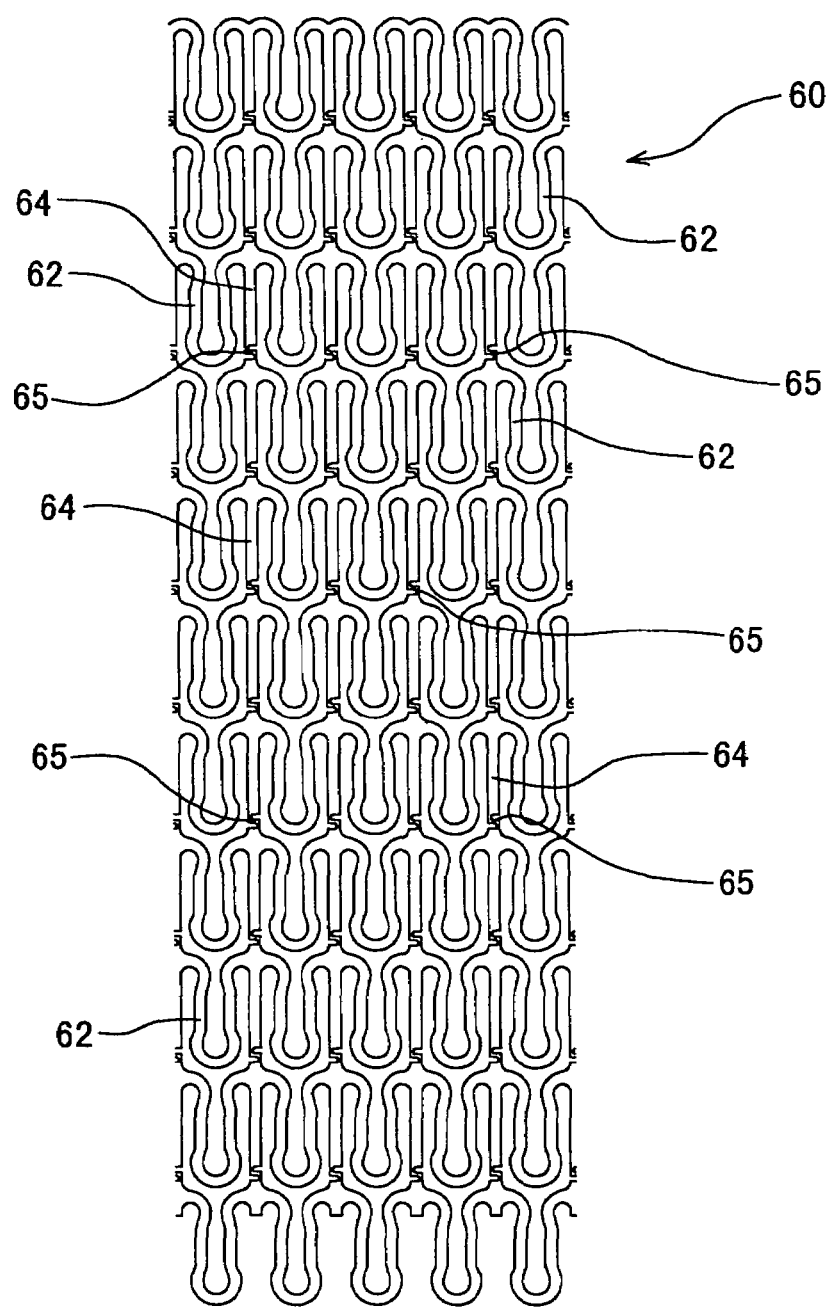
FIG. 9 is a development view of the stent of FIG. 8.
Figure 10:
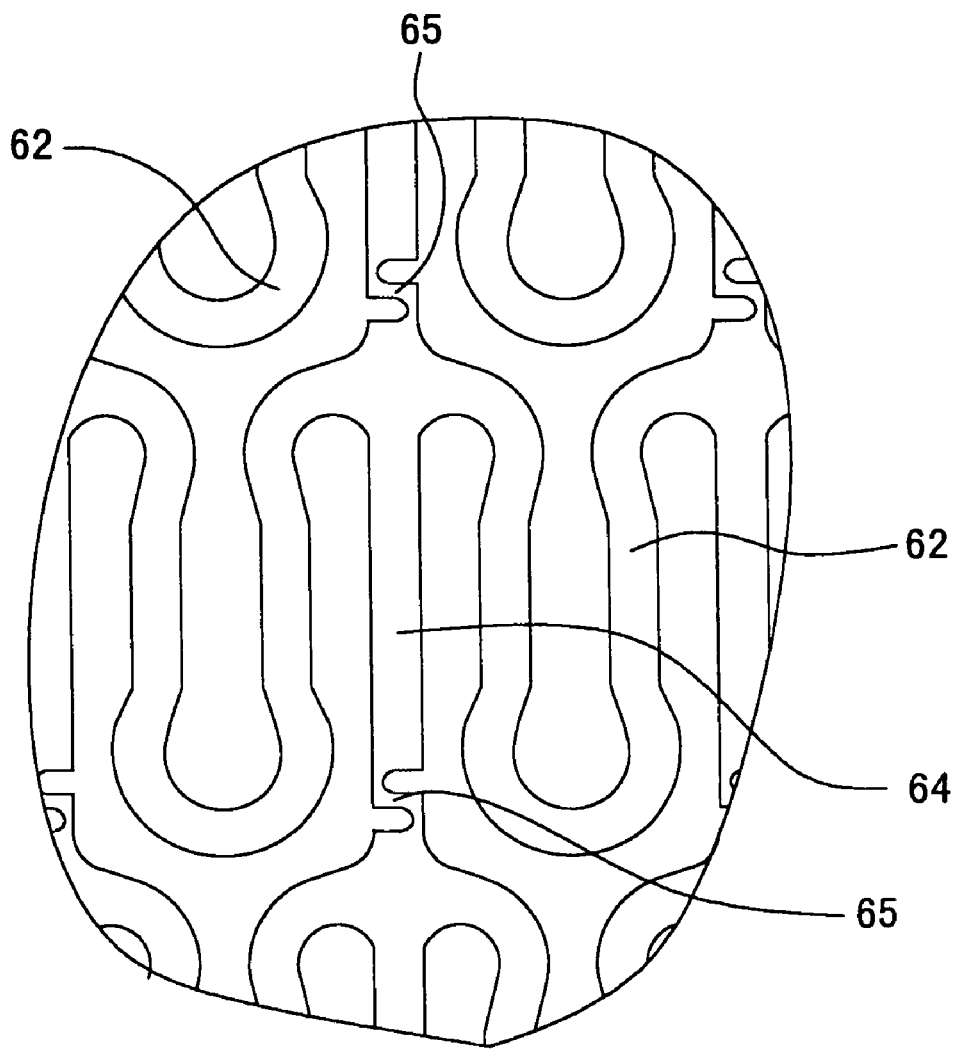
FIG. 10 is a partly enlarged front view of the stent of FIG. 8.
Figure 11:
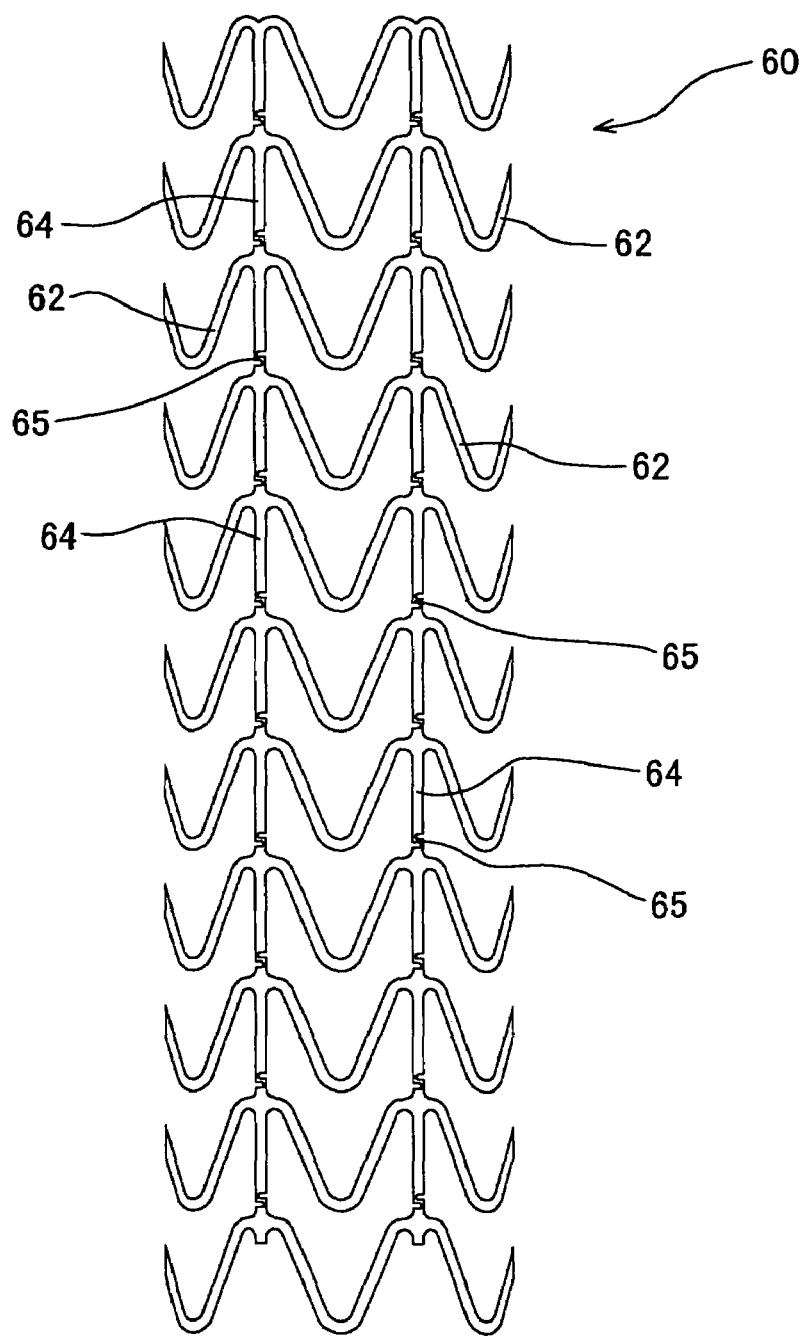
FIG. 11 is a front view of the dilated stent of FIG. 8.
Figure 12:
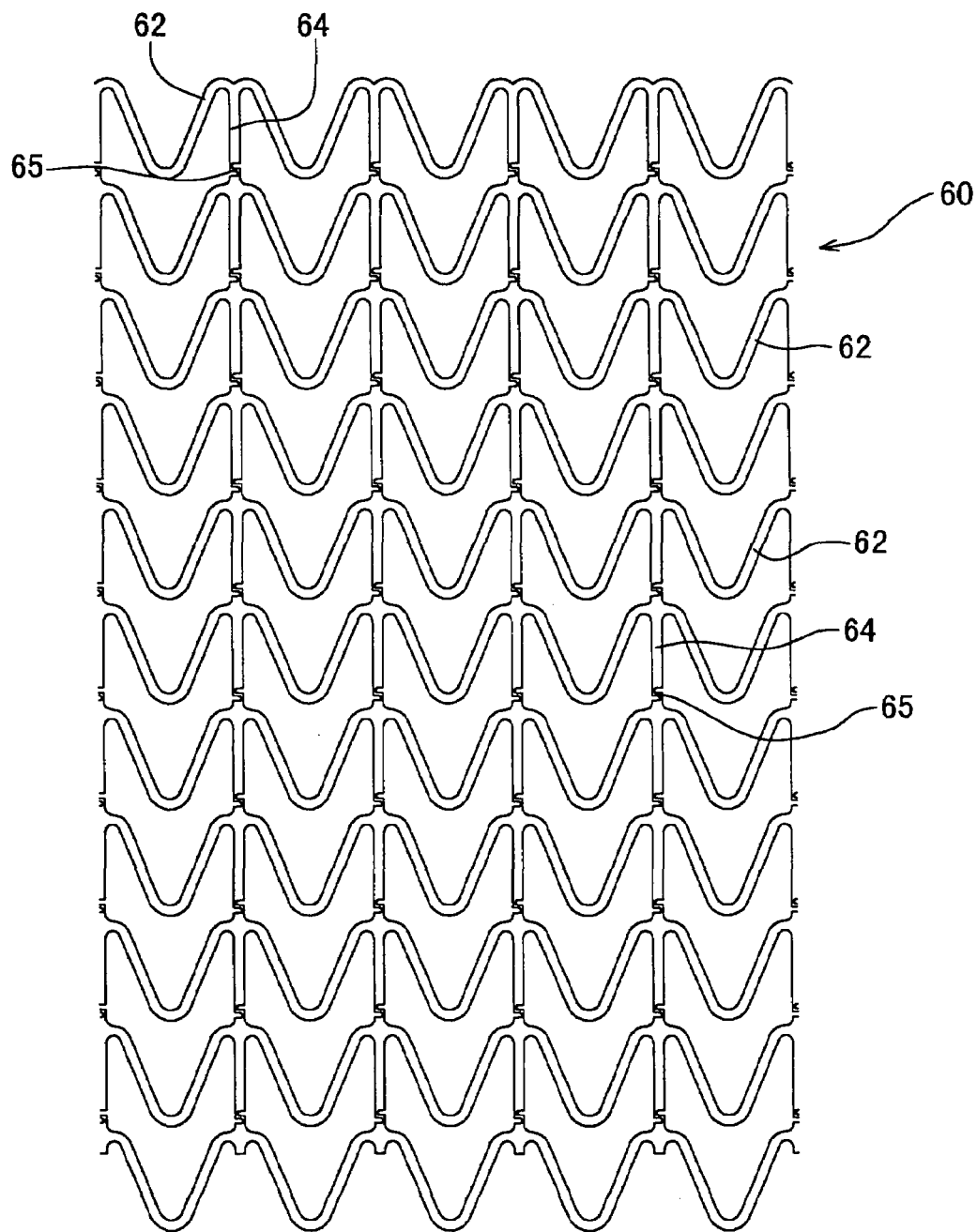
FIG. 12 is a development view of the dilated stent of FIG. 11.
Figure 13:
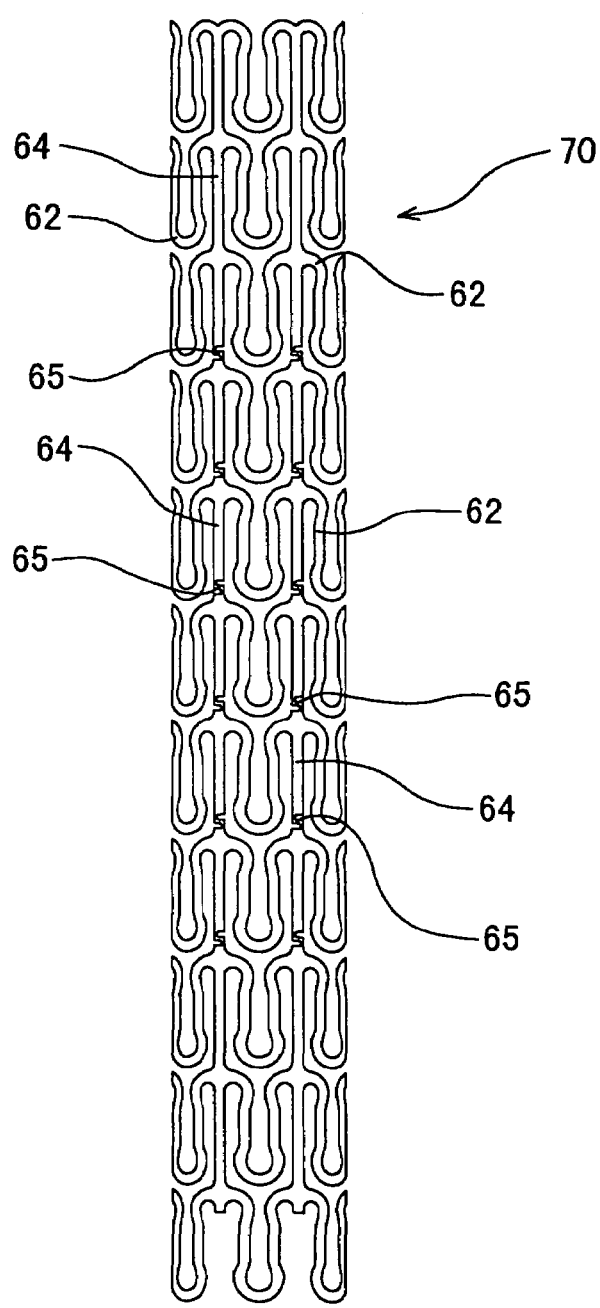
FIG. 13 is a front view of a stent according to another embodiment of the present invention.

FIG. 8 is a front view of a stent according to still another embodiment of the present invention. FIG. 9 is a development view of the stent of FIG. 8. FIG. 10 is a partly enlarged front view of the stent of FIG. 8. FIG. 11 is a front view of the dilated stent of FIG. 8. FIG. 12 is a development view of the dilated stent of FIG. 11. FIG. 13 is a front view of a stent according to another embodiment of the present invention.

In a stent 60 of the embodiment, as shown in FIGS. 8 through 10, a plurality of wavy annular members 62 are adjacently formed such that mountains and valleys thereof are arranged approximately linearly, respectively in the axial direction of the stent 60. A connection portion 64 connects mountains (valleys) of the adjacent wavy annular members 62 to each other. The connection portions 64 located in the vicinity of the axial center of the stent 60 have a weak portion 65, respectively.

In other words, the stent 60 has a plurality of the annular members 62 made of a (endless) linear material connected to each other wavily (zigzag) and annularly. The annular member 62 serve as a means of keeping the stent 60 dilated. The connection portion (connector) 64 connects the adjacent annular members to each other to prevent them from separating from each other. A weak portion 65 (cutting point) is formed on the connection portion 64. The weak portion 65 is formed not on the annular member 62 but on the connection portion 64. In other words, the weak portion 65 is not formed on the annular member 62. If the weak portion 65 is formed on the annular member 62, the annular member may be naturally broken when the stent 60 is dilated. That is, if the annular member 62 has the weak portion 65 formed thereon, they may have a low dilating force when the stent 60 is dilated. But even though the weak portion 65 is formed on the connection portion 64, the connection portion 64 hardly deforms when the stent 60 is dilated. Thus, the weak portion 65 is hardly broken naturally when the stent 60 is dilated. Although each connection portions 64 has the weak portion 65 in the embodiment, it is possible to form the weak portion 65 on only the connection portion located in the vicinity of the axial center of the stent 60. The weak portion may be formed at any position of the connection portion 64. In the embodiment, the weak portion is formed on the connection portion 64 such that the weak portion is located proximately to the mountain of the adjacent annular member 62. However, the weak portion may be formed in the vicinity of the axial center of the connection portion 64.

The weak portion 65 has a smaller than sectional area than the other constituent parts of the stent 60. Specifically, a nick is formed on each of the opposite side surfaces of the connection portion 64 such that the nicks are axially spaced at a certain interval. In this manner, the weak portion 65 can be securely formed on the connection portion 64. In addition to this construction, any construction of the weak portion 65 can be adopted so long as it can be destroyed when a force is applied thereto. As an example, one nick is formed on one side surface of the connection portion such that the nick extends to the widthwise center thereof. As another example, two nicks are formed on both side surfaces of the connection portion such that the nicks extend to the widthwise center thereof and confront each other. As still another example, a portion is formed on the connection portion such that the portion is shorter or thinner than other portions thereof. As still another example, a portion is formed on the connection portion such that the portion is shorter and thinner than other portions thereof.

An inflating balloon catheter can be inserted into the stent 60 of the embodiment such that the inflating balloon catheter penetrates through a side wall of the stent from its interior after the stent is dilated radially. The weak portion 65 of the connection portion 64 can be broken by the inflation of the balloon of the inflating balloon catheter. As shown in FIGS. 11 and 12, each annular member keeps a dilated configuration. Thus the entire stent 60 also keeps a dilated configuration. When the inflating balloon catheter is inserted into the dilated stent and passed the side wall of the stent 60 by guiding with a guide wire and the balloon is inflated, the connection portion 64 of the stent is cut off at the weak portion (cutting point) 65 by the inflated balloon. As a result, a hole having a diameter almost equal to an enlarged diameter of the inflated balloon is formed through the side wall. If the stent does not have the the weak portion (cutting point) 65, the inflating-balloon catheter cannot secure a hole (space) larger than the space formed of a deformation of the annular members to the maximum. Thus, if the stent is dilated forcibly, the balloon bursts.

The stent is not limited to the above-described modes. For example, as shown in FIG. 13, the weak portion 65 may be formed on only the connection portion 64 located in the vicinity of the axial center of the stent. As another mode or construction of the stent, the valleys of the adjacent wavy annular members may be connected to each other (this construction can be formed by inverting the stent shown in FIG. 8 axially). As still another example, the stent may be so constructed that connection portions located at odd-numbered positions in the axial direction of the stent connect the mountains to each other and connection portions located at even-numbered positions in the axial direction thereof connect the valleys to each other. Alternatively, the stent may be so constructed that connection portions located at odd-numbered positions in the axial direction of the stent connect the valleys to each other and connection portions located at even-numbered positions in the axial direction thereof connect the mountains to each other.

Similarly to the stent 1, in the stent 60, to reduce the degree of damage to be applied to the inflated balloon when the connection portion 4 is broken, it is preferable that the edge of the wavy element of the stent is chamfered. As the method of chamfering the stent, after the stent is fabricated into a final shape, chemical polishing, electropolishing or mechanical polishing can be used. Similarly to the stent 1, in the stent 60, it is possible that the wavy element of the annular members located at the opposed ends of the stent in the axial direction thereof has a sectional area, respectively smaller than that of the other wavy annular members. Further, similarly to the stent 1, it is possible that the material of the annular unit located at the axial center of the stent 1 have the maximum cross-sectional area. It is also possible that the annular units located nearer to the axial end of the stent have a smaller cross-sectional area than the annular units located nearer to the axial center of the stent.

It is preferable that the material of the stent 60 has a certain degree of compatibility with an organism. For example, it is possible to use stainless steel, tantalum or tantalum alloys, platinum or platinum alloys, gold or gold alloys, cobalt base alloys and the like. It is preferable to plate the stent with a noble metal such as gold and platinum after the stent is fabricated into a final shape. As the stainless steel, SUS 316L most corrosion-resistant of the above metals can be preferably used. Similarly to the stent 1, it is preferable to anneal the stent 60 after it is fabricated into the final shape.

The stent 60 has a diameter favorably 0.8 to 1.8 mm and more favorably 1.0 to 1.6 mm in an undilated state. The stent 60 has a length favorably 7 to 25 mm in an undilated state. The length of the wavy annular member 62 has a length of 0.7 to 2.0 mm. The length of one connection portion 64 is favorably 0.9–2.5 mm. The number of the wavy annular members 62 is four to seven. The distance between the center of one annular member 62 and that of the annular member adjacent thereto is preferably 0.9 to 2.5 mm.

The thickness of the wavy annular member 62 of the stent 60 and that of the connection portion 64 are favorably 0.05 to 0.15 mm and more favorably 0.08 to 0.12 mm. The width of the wavy annular member 62 and that of the connection portion 64 are favorably 0.07 to 0.15 mm and more favorably 0.08 to 0.12 mm. The length (width) of the narrowest portion (weak portion) of the connection portion 64 of the stent 60 is favorably 0.01–0.05 mm. The sectional area of the weak portion is favorably 1/50 to 1/2 of that of the other parts and more favorably 1/20 to 1/10 of that of the other parts.

Another embodiment of the present is described below with reference to the drawings.

Figure 20:
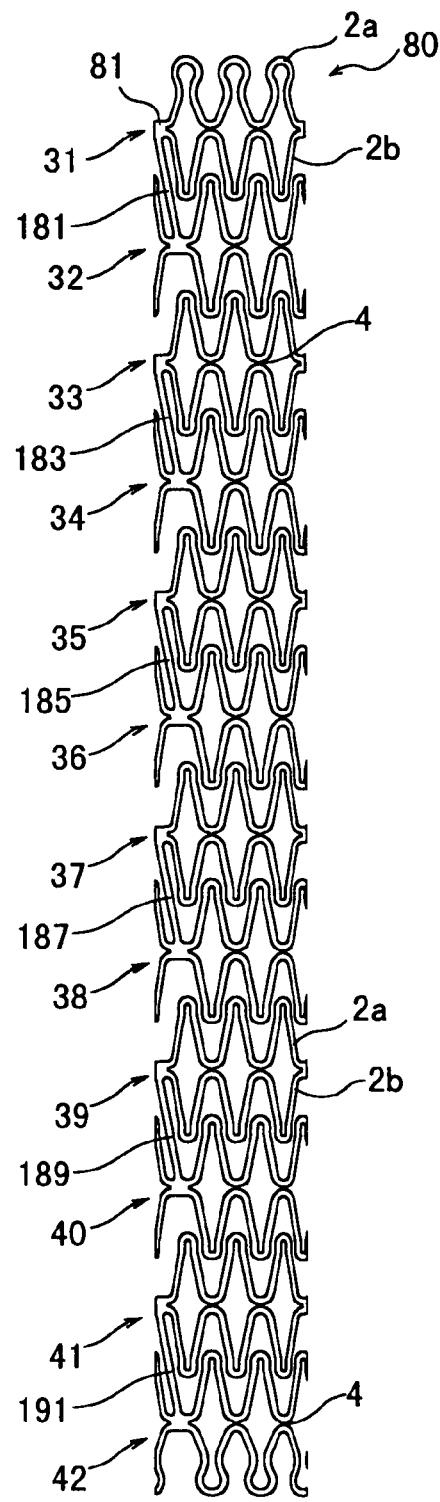
FIG. 20 is a front view of a stent according to another embodiment of the present invention.
Figure 21:
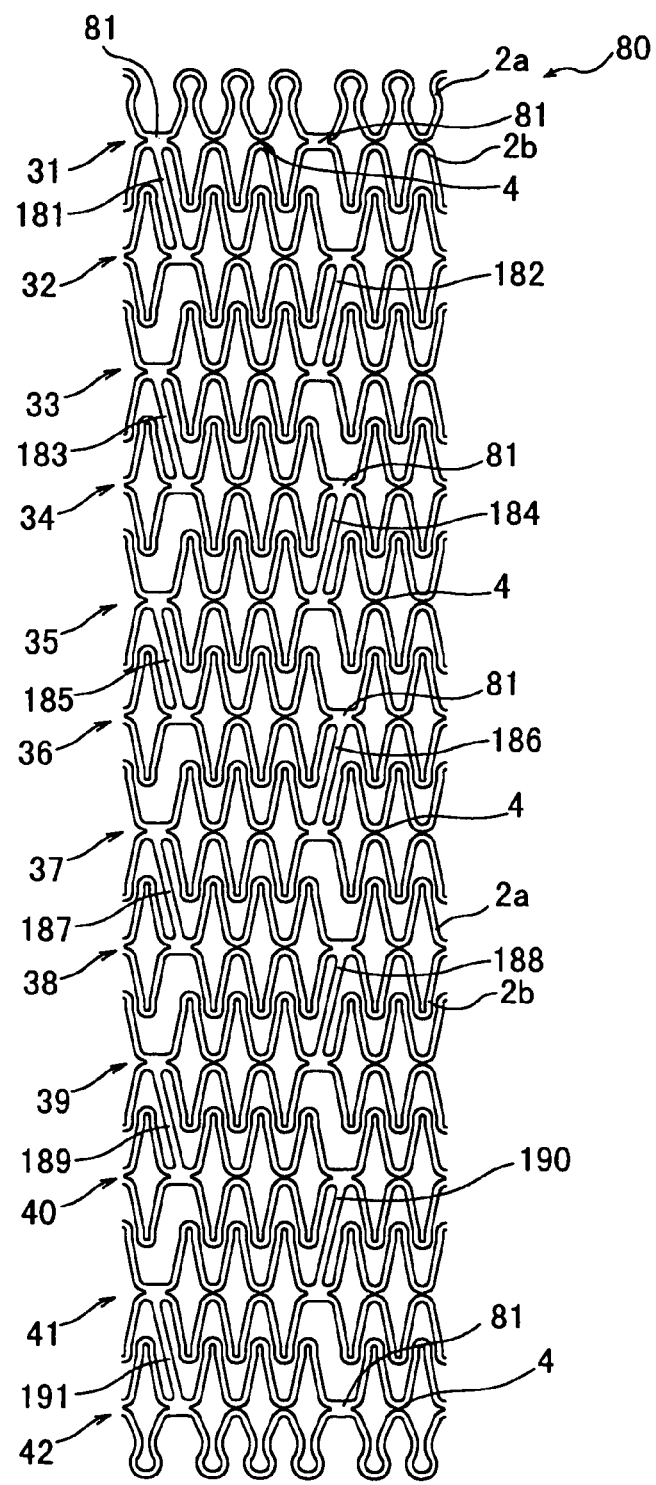
FIG. 21 is a development view of the stent of FIG. 20.
Figure 22:
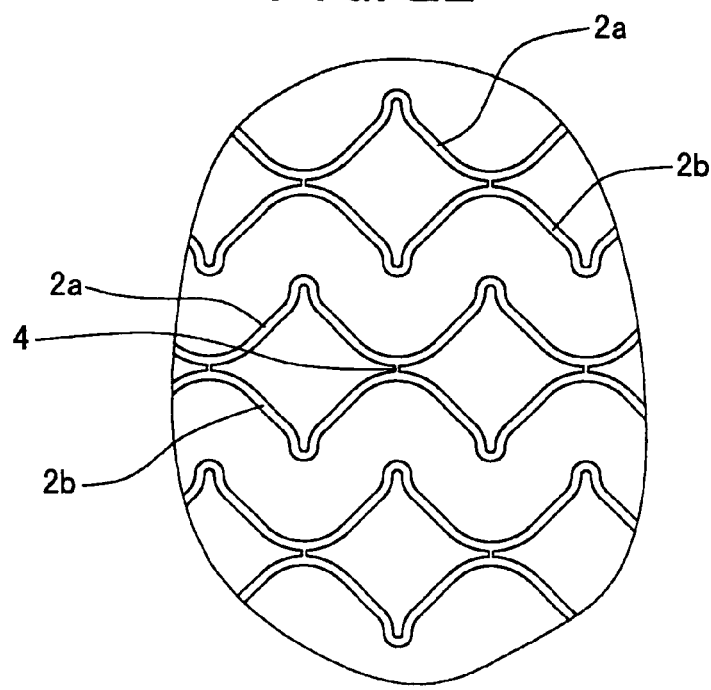
FIG. 22 is a partly enlarged front view of the dilated stent of FIG. 20.
Figure 23:
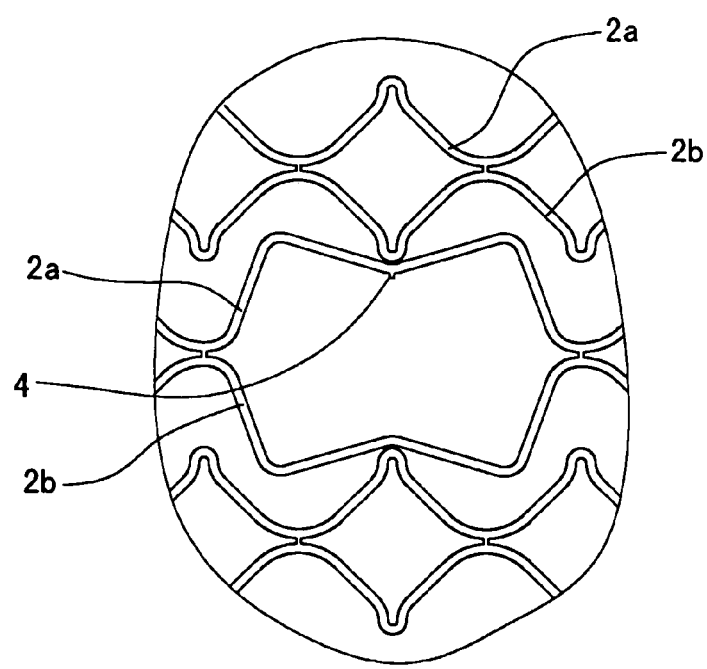
FIG. 23 is a partly enlarged front view of the dilated stent, of FIG. 20, whose connection portion is broken.

FIG. 20 is a front view of a stent according to another embodiment of the present invention. FIG. 21 is a development view of the stent of FIG. 20. FIG. 22 is a partly enlarged front view of the dilated stent of FIG. 20. FIG. 23 is a partly enlarged front view of the dilated stent, of FIG. 20, whose connection portion is broken.

A stent 80 of the present invention is a so-called balloon expandable stent. That is, the stent 80 is formed in a substantially tubular configuration and has a diameter so set that the stent 80 is inserted into the body. The stent 80 can be dilated radially outwardly upon application of a force acting radially outwardly from the interior of the tubular stent.

The stent 80 has a plurality of wavy annular members (wavy line-shaped annular member) 2a, 2b each formed of a narrow wavy element and arranged in the axial direction thereof; and a plurality of connection portions 4 each connecting the adjacent wavy annular members 2a, 2b to each other axially. The connection portion 4 located in the vicinity of the axial center of the stent 80 is weaker than the other constituent parts and can be broken. Owing to the construction, an inflating balloon catheter can be inserted into the stent 80 such that the inflating balloon catheter penetrates through a side wall of the stent from its interior after the stent is dilated radially. The connection portion 4 can be broken by the inflation of the balloon of the inflating balloon catheter.

Specifically, as shown in FIGS. 20 through 22, the stent 80 comprises a plurality of annular units 31, 32, 33, 34, 35, 36, 37, 38, 39, 40, 41 and 42 and joining portions 181, 182, 183, 184, 185, 186, 187, 188, 189, 190 and 191. The annular units 3142 consists of the first wavy annular member 2a formed of a narrow wavy element (preferably, having no edge); the second wavy annular member 2b disposed in the axial direction of the stent 80 such that a mountain of the second wavy annular member 2b is proximate to a valley of the first wavy annular member 2a and formed of a narrow wavy element (preferably, having no edge); a plurality of connection portions 4 (preferably, having no edge) each connecting the valley of the first wavy annular member 2a and the mountain of the second wavy annular member 2b to each other; and an integral portion (fused portion) 81 consisting of the valley of the first wavy annular member 2a and the mountain of the second wavy annular member 2b integrated (fused) therewith. A plurality of annular units is arranged approximately linearly in the axial direction of the stent 80. Each of the annular units has one of narrow joining portions 181–191 (preferably, having no edge) each connecting the wavy elements (wavy annular member 2a, 2b) of the adjacent annular units to each other to thereby form the cylindrical stent. Each of the annular units has two integral portions. The two integral portions are so disposed that the adjacent ones are not continuous with each other. The joining portions 181–191 are so disposed that they connect the integral portions (fused portion) 81 to each other. Only one joining portion 181–191 is formed between the adjacent annular units. The joining portions 181–191 are so disposed that the adjacent ones are not continuous with each other. The joining portions 181–191 are so formed that they orient in different directions alternately in the axial direction of the stent.

The manner of disposing the integral portion (fused portion) 81 is not limited to the above-described one. Also, the configuration of the joining portion is not limited to the above-described one. For example, the integral portion (fused portion) 81 may be disposed spirally, and the joining portion connecting the integral portions (fused portion) 81 to each other may be disposed also spirally.

In the stent 80, the connection portion 4 located in the vicinity of the axial center of the stent 80 is weaker than the other constituent parts and can be broken. In other words, the stent 80 is a tubular body comprising a large number of annular units connected to each other with the connection portions.

As shown in FIGS. 20 and 21 which is a developed view of FIG. 20, each of the annular members 2a, 2b of the stent 80 has six mountains and valleys spaced at almost the same intervals except the integral poritons. Each of the annular members 2a, 2b is formed of a plurality of the wavy elements having no edge. It is preferable that the number of the mountains (valleys) of the annular member is four to eight. The second wavy annular member 2b is disposed in the axial direction of the stent 80 such that the mountain thereof is proximate to the valley of the first wavy annular member 2a. The mountain of the second wavy annular member 2b and the valley of the first wavy annular member 2a are integral with each other partly through the integral portion (fused portion) 81. In the portions of the first and second wavy annular members 2a and 2b other than the integral portion (fused portion) 81, the valley of the first wavy annular member 2a and the mountain of the second wavy annular member 2b are connected to each other with a plurality of the short connection portions 4 to form one annular unit. In the embodiment, all the valleys of the first wavy annular member 2a and all the mountains of the second wavy annular member 2b are connected to each other with the connection portions 4 except the integral portion (fused portion) 81. One annular unit has four (less by two than the number of mountains or valleys of annular member) connection portions 4.

The connection portion 4 located in the vicinity of the axial center of the stent 80 is weaker than other constituent parts of the stent 80 and can be broken. As shown in FIGS. 20 through 22, in the stent 80 of the embodiment, the sectional area of each connection portion 4 has a smaller (in other words, narrower) sectional area than that of each of the other parts of the stent 80, namely, the wavy annular members 2a, 2b and the joining portions 181–191. That is, the connection portion 4 is weaker than the other parts of the stent 80. In particular, in the embodiment, the thickness of the connection portion 4 is almost equal to that of the other parts but the width thereof is smaller than that of the other parts.

The annular members 2a, 2b are formed not weakly but the connection portion 4 is formed weakly. A weak portion is not formed on the annular members 2a, 2b. If the weak portion is formed on the annular members 2a, 2b, the annular members 2a, 2b may be naturally broken when the stent 80 is dilated. That is, if the annular members 2a, 2b have the weak portion formed thereon, they may have a low dilating force. But even though the connection portion 4 is formed weakly, the connection portion 4 hardly deforms when the stent 80 is dilated. Thus, the connection portion 4 is hardly broken naturally when the stent 80 is dilated.

Although all the connection portions 4 of the stent 80 are weak, it is possible to form a weak connection portion 4a only in the vicinity of the axial center of the stent 50, as in the case of the stent shown in FIG. 7. The length of the region in which the weak connection portion is formed is preferably 30–60% of the entire length of the stent 50. The region in which the weak connection portion is formed is so formed that the center thereof is located at approximately the center of the stent in the axial direction thereof. In the embodiment shown in FIG. 7, the connection portion 4b located in the vicinity of each axial end of the stent has a width equal to that of the wavy element of each of the annular members 2a, 2b and does not have the weak portion.

Further, instead of making the entire connection portions 4 weak, as in the case of the stent shown in FIGS. 8 through 12, it is possible to form a weak portion on the connection portions 4 such that a portion having a smaller sectional area than the other constituent parts of the stent is formed on the connection portions 4 having the same sectional area as those of the other component parts. As the mode of the weak portion, for example, a nick is formed on each of the opposite side surfaces of the connection portion such that the nicks are axially spaced at a certain interval. As another example, one nick is formed on one side surface of the connection portion such that the nick extends to the widthwise center thereof. As still another example, two nicks are formed on both side surfaces of the connection portion such that the nicks extend to the widthwise center thereof and confront each other. As further example, a portion is formed on the connection portion such that the portion is shorter or thinner than other portions thereof. As still further example, a portion is formed on the connection portion such that the portion is shorter and thinner than other portions thereof.

In the stent 80 of the present invention, an inflating balloon catheter can be inserted into each of the stents such that the inflating balloon catheter penetrates through a side wall of the stent from its interior after the stent is dilated radially. The connection portion can be broken by the inflation of the balloon of the inflating balloon catheter, as shown in FIG. 23. As shown in FIG. 23, each annular member keeps a dilated configuration. Thus the entire stent 80 also keeps a dilated configuration. When the inflating balloon catheter is inserted into the dilated stent and passed the side wall of the stent 80 by guiding with a guide wire and the balloon is inflated, the connection portion of the stent is cut off at the weak portion by the inflated balloon. As a result, a hole having a diameter almost equal to an enlarged diameter of the inflated balloon is formed through the side wall. If the stent does not have the the weak portion, the inflating balloon catheter cannot secure a hole (space) larger than the space formed of a deformation of the annular members to the maximum. Thus, if the stent is dilated forcibly, the balloon bursts. That is, because the stent has the weak connection portion, the stent is stable in its configuration in a blood vessel.

The joining portions 181–191 joining the wavy annular members of the adjacent annular units 31–42 remain unchanged substantially in their lengths when the stent 80 is dilated. Because the joining portions 181–191 and the connection portion 4 remain substantially unchanged in their lengths even when the stent 80 is dilated, the overall length of the stent 80 remains substantially unchanged before and after dilation. It never happens that the stent is reduced in length after dilation.

The joining portion 181–191 is so disposed that it connects the adjacent annular units 31–42 at only one position. Although the adjacent annular units 31–42 may be connected at two or more positions, it is preferable to connect them at only one position as embodied in the present invention so that the stent follows deformation of a blood vessel faithfully. Further in the embodiment, the joining portion 181–191 may be so disposed that the adjacent ones are continuous with each other.

To reduce the degree of damage to be applied to the inflated balloon when the connection portion 4 is broken, it is preferable that the edge of the wavy element of the stent is chamfered. As the method of chamfering the stent, after the stent is fabricated into a final shape, chemical polishing, electropolishing or mechanical polishing can be used. The chemical polishing is preferably carried out by dipping the stent in a chemical polishing solution for stainless steel. Any chemical polishing solution containing one capable of dissolving stainless steel may be used. For example, one preferable chemical polishing solution contains a mixture of hydrochloric acid and nitric acid serving as a base component and additives such as an organic sulfur compound for adjusting a dissolution rate, smoothing, and imparting luster and a surface active agent.

It is possible that the wavy element of the annular members 2a, 2b located at the opposed ends of the stent 80 in the axial direction thereof has a sectional area, respectively smaller than that of the other wavy annular members. This construction causes the dilation force of the wavy annular members located at the opposed ends of the stent 80 in the axial direction thereof to be lower than those of the other wavy annular members when the stent 80 dilates, but allows the annular members 2a, 2b located at the opposed ends of the stent 80 in the axial direction thereof to follow the bending of a blood vessel to a high extent. That is, the opposed ends of the stent 80 in the axial direction thereof have a high degree of affinity for the blood vessel. As the method of reducing the thickness of the annular members 2a, 2b located at the opposed ends of the stent 80 in the axial direction thereof, after the stent is fabricated into the final shape, the annular members 2a, 2b is chemically polished or mechanically polished.

It is possible that the material of the annular unit (annular member) located at the axial center of the stent 80 have the maximum cross-sectional area and that the annular units (annular member) located nearer to the axial end of the stent have a smaller cross-sectional area than the annular units located nearer to the center of the stent. Specifically, the thickness of the annular units are so set that the thickness of the annular units 34, 35, 36, 37 and 38 located at the axial central part of the stent 80 have a largest thickness and the other annular units have small thicknesses decreasingly as they are nearer to both axial ends of the stent. This construction ensures that the stent 80 displays a sufficient dilating force at its central part and faithfully follows a bent portion of a blood vessel. That is, both axial ends of stent 80 have better affinity for the blood vessel. It is also possible that the annular unit located at the center of the stent 80 has a maximum width and the other annular units have small widths decreasingly as they are nearer to both axial ends of the stent.

In the stent 80, a part of the wavy annular member 2a of one annular unit is in penetration into the wavy space formed at the axial end (inner side of stent) of the other annular unit adjacent to the one annular unit. That is, a part of the mountain of the wavy annular member 2a of one annular unit is in penetration into the concave portion of the wavy annular member 2b formed in the vicinity of the connection portion of the other annular unit adjacent to the one annular unit. Therefore, the adjacent annular units overlap partially each other when the stent 80 is viewed in the axial direction thereof. Thus, when the constituent elements of the wavy annular members are reduced in their lengths in the axial direction of the stent upon dilation of the stent, gaps on the side surface of the stent increase to a small extent. Therefore, it is possible to dilate a stenosed portion of a blood vessel securely and holds an affected portion without a gap.

The mountain of the annular member 2b having one of the joining portions 181–191 formed therein is wider than the other mountains thereof, such that a part of the mountain is adjacent to the joining portion. Similarly, the valley of the annular member 2a having one of the joining portions 181–191 formed therein is wider than the other valleys thereof, such that a part of the valley is adjacent to the joining portion. In the embodiment, the joining portion is approximately linear.

It is preferable that the material of the stent 80 has a certain degree of compatibility with an organism. For example, it is possible to use stainless steel, tantalum or tantalum alloys, platinum or platinum alloys, gold or gold alloys, cobalt base alloys and the like. It is preferable to plate the stent with a noble metal such as gold and platinum after the stent is fabricated into a final shape. As the stainless steel, SUS 316L most corrosion-resistant of the above metals can be preferably used.

It is preferable to anneal the stent 80 after it is fabricated into the final shape. Annealing improves the flexibility and plasticity of the entire stent so that the stent can be effectively implanted in a curved blood vessel. As compared with a non-annealed stent, the annealed stent has a lower force of restoring to an original state after it is dilated, and especially has a lower force of restoring to an original linear state when it is dilated at a curved portion of a blood vessel. This minimizes physical stimulation to the inner wall of the curved blood vessel, thus reducing the cause of a recurrence of stenosis. The stent is preferably annealed by heating it to 900 to 1200° C. in an inert gas atmosphere (e.g., a mixture gas of nitrogen and hydrogen) so that no oxide film is formed on the surface of the stent and then slowly cooling it.

The stent 1 has a diameter favorably 0.8 to 1.8 mm and more favorably 1.0 to 1.6 mm in an undilated state. The stent 80 has a length favorably 9 to 40 mm in an undilated state. The length of each of the wavy annular members 2a, 2b has a length of 0.7 to 2.0 mm. The length of one of the annular units 31 through 42 is favorably 1.5–4.0 mm and more favorably 2.0–3.0 mm. The length of one connection portion 4 is favorably 0.01–0.5 mm. The number of the annular units is 3 to 50. The constituent elements (annular member) of the adjacent annular units have an axial overlap of about 0.5 to 1 mm. The distance between the center of one annular units and that of the annular unit adjacent thereto is preferably 1.3 to 2.5 mm. The length of each of the joining portions 181–191 is preferably 1.4 to 2.7 mm. The angle of inclination (the angle of inclination of the joining portion relative to a longitudinal direction in a development view) of each of the joining portion 181 through 191 relative to the axis of the stent is favorably 0° to 30° and more favorably 5° to 25°.

The thickness of each of the wavy annular members (wavy elements, wavy line-shaped elements) 2a, 2b of the stent 80 and that of each of the joining portions 181–191 are favorably 0.05 to 0.15 mm and more favorably 0.08 to 0.12 mm. The width of each of the wavy annular members 2a, 2b and that of each of the joining portions 181–191 are favorably 0.07 to 0.15 mm and more favorably 0.08 to 0.12 mm. The thickness of the connection portion 4 of the stent 80 is favorably 0.05–0.12 mm and more favorably 0.06–0.10 mm. The width of the connection portion 4 of the stent 80 is favorably 0.01–0.05 mm and more favorably 0.02 to 0.04 mm. The sectional area of the connection portion 4 is favorably 1/50 to 1/2 of that of the other parts (annular member and joining portion) and more favorably 1/20 to 1/10 of that of the other parts.

Another embodiment of the present is described below with reference to the drawings.

Figure 24:
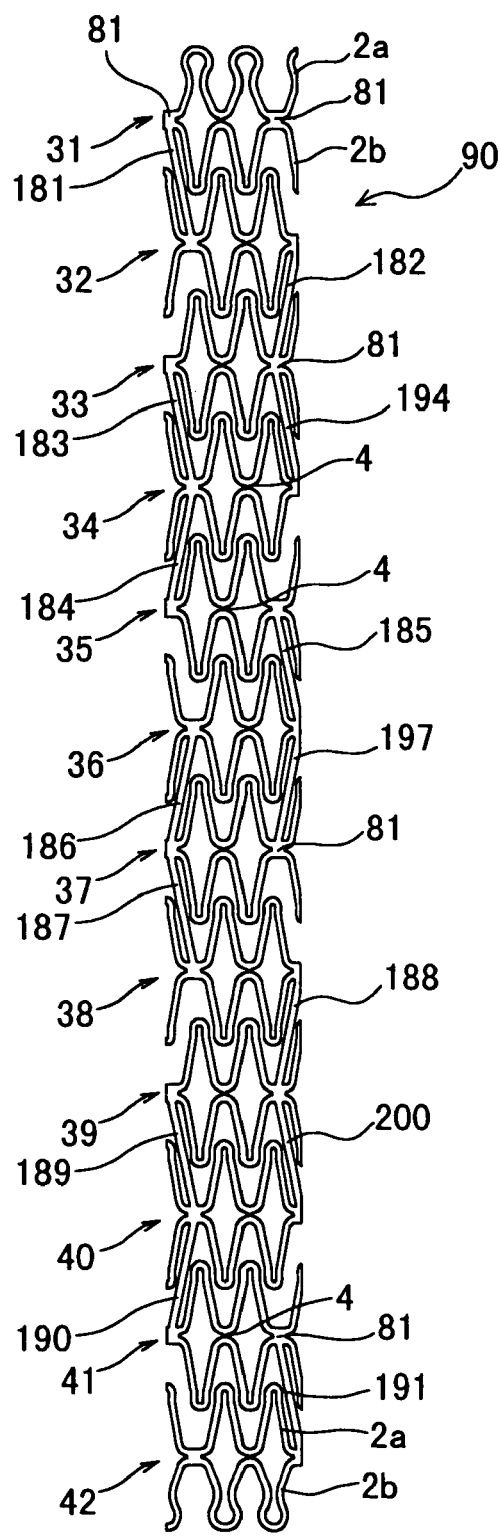
FIG. 24 is a front view of a stent according to another embodiment of the present invention.
Figure 25:
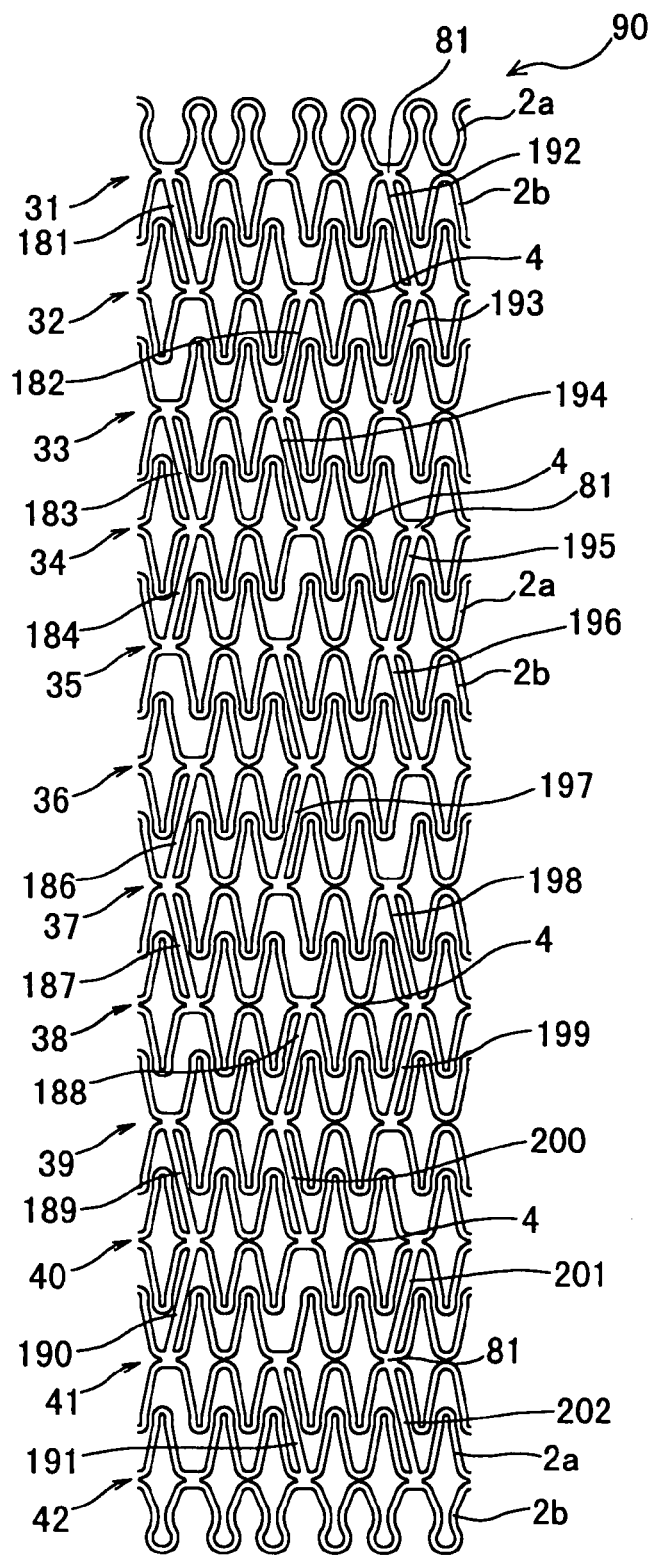
FIG. 25 is a development view of the stent of FIG. 24.

FIG. 24 is a front view of a stent according to another embodiment of the present invention. FIG. 25 is a development view of the stent of FIG. 24. FIG. 22 is referred as a partly enlarged front view of the enlarged stent of FIG. 24. FIG. 23 is also referred as a partly enlarged front view of the dilated stent, of FIG. 24, whose connection portion is broken.

A stent 90 of the present invention is a so-called balloon expandable stent. That is, the stent 90 is formed in a substantially tubular configuration and has a diameter so set that the stent 90 is inserted into the body. The stent 90 can be dilated radially outwardly upon application of a force acting radially outwardly from the interior of the tubular stent.

The stent 90 has a plurality of wavy annular members (wavy line-shaped annular member) 2a, 2b each formed of a narrow wavy element and arranged in the axial direction thereof; and a plurality of connection portions 4 each connecting the adjacent wavy annular members 2a, 2b to each other axially. The connection portion 4 located in the vicinity of the axial center of the stent 80 is weaker than the other constituent parts and can be broken. Owing to the construction, an inflating balloon catheter can be inserted into the stent 80 such that the inflating balloon catheter penetrates through a side wall of the stent from its interior after the stent is dilated radially. The connection portion 4 can be broken by the inflation of the balloon of the inflating balloon catheter.

Specifically, as shown in FIGS. 24 and 25, the stent 90 comprises a plurality of annular units 31, 32, 33, 34, 35, 36, 37, 38, 39, 40, 41 and 42 and joining portions 181, 182, 183, 184, 185, 186, 187, 188, 189, 190, 191, 192, 193, 194, 195, 196, 197, 198, 199, 200, 201 and 202. The annular units 31–42 each have the first wavy annular member 2a formed of a narrow wavy element (preferably, having no edge); the second wavy annular member 2b disposed in the axial direction of the stent 90 such that a mountain of the second wavy annular member 2b is proximate to a valley of the first wavy annular member 2a and formed of a narrow wavy element (preferably, having no edge); a plurality of narrow connection portions 4 (preferably, having no edge) each connecting the valley of the first wavy annular member 2a and the mountain of the second wavy annular member 2b to each other; and an integral portion (fused portion) 81 consisting of the valley of the first wavy annular member 2a and the mountain of the second wavy annular member 2b integrated (fused) therewith. A plurality of annular units is arranged approximately linearly in the axial direction of the stent 90. Each of the annular units has one of joining portions 181–202 (preferably, having no edge) each connecting the wavy elements of the adjacent annular units to each other. Thereby, the cylindrical stent is formed. One annular unit has three integral portions. The three integral portions are so formed that they are not adjacent to each other. The joining portions 181–202 are so formed that they connect the integral portions (fused portions) 81 to each other. The joining portions 181–202 are so formed that two of them are disposed between the adjacent annular units. The joining portions 181–202 are so arranged that those adjacent to each other are continuous with each other. However, the joining portions 181–202 are so arranged that two of them are continuous with each other and more than two of them are not continuous with each other. The joining portions 181–202 are so formed that they orient in different directions alternately in the axial direction of the stent. The joining portions connecting the adjacent annular units to each other orient in the same direction in the axial direction of the stent. As shown in FIGS. 24 and 25, the continuous joining portions are bent at a certain portion. The continuous joining portions can be called a joining portions-continuous member. For example, a joining portions-continuous member is consisted by the joining portions 182 and 194. The joining portions-continuous member connects three annular units to each other. The joining portions-continuous member is bent at its center. For example, the joining portions-continuous member is bent between the joining portions 182 and 194. More specifically, the joining portions-continuous member is bent at the integral portion of the central annular unit of the continuous three annular units. The adjacent joining portions-continuous members have different bending directions. The alternate joining portions-continuous members have the substantially same bending direction. Each joining portions-continuous member is disposed by forming an angle 120' between the joining portions-continuous member and the axis of the stent. For example, the joining portions-continuous member consisting of the joining portions 182 and 194 is disposed by forming an angle 120' between the joining portions-continuous member consisting of the joining portions 183 and 184 and the axis of the stent 90. Further, the joining portions-continuous members are dislocated from each other by the length of one joining portion (half of joining portions-continuous member) in the rear-end direction of the stent. For example, the joining portions-continuous member consisting of the joining portions 183 and 184 is dislocated from the joining portions-continuous member consisting of the joining portions 182 and 194 by the length of the joining portion 194.

Thus, the joining portions-continuous members are disposed spirally on the outer surface of the stent. In the adjacent annular units except the annular units 31 and 42 disposed at both axial ends of the stent 90, there is disposed the rear side (rear half of joining portions-continuous member) of one joining portions-continuous member and the front side (front half of joining portions-continuous member) of the other joining portions-continuous member (located adjacent to the one joining portions-continuous member). Thus, one joining portion (half of joining portions-continuous member) of one joining portions-continuous member and one joining portion of the other joining portions-continuous member overlap each other in the axial direction of the stent. In other words, the joining portions-continuous members do not overlap each other entirely in the axial direction of the stent.

Owing to the arrangement of the joining portions (joining portions-continuous members), the stent has a cylindrical configuration-holding force to a high extent when the stent is dilated diametrically. Further, the joining portions arranged in this manner prevent the stent from being bent in a particular direction to a high extent.

The manner of disposing the integral portion (fused portion) 81 is not limited to the above-described one. Also, the configuration of the joining portion is not limited to the above-described one.

In the stent 90, the connection portion 4 located in the vicinity of the axial center of the stent 90 is weaker than the other constituent parts and can be broken. In other words, the stent 90 is a tubular body comprising a large number of annular units connected to each other with the connection portions.

As shown in FIGS. 24 and 25 which is a developed view of FIG. 24, each of the annular members 2a, 2b of the stent 90 has six mountains and valleys spaced at almost the same intervals except the integral portions. Each of the annular members 2a, 2b is formed of a plurality of the wavy elements having no edge. It is preferable that the number of the mountains (valleys) of the annular member is four to eight. The second wavy annular member 2b is disposed in the axial direction of the stent 90 such that the mountain thereof is proximate to the valley of the first wavy annular member 2a. The mountain of the second wavy annular member 2b and the valley of the first wavy annular member 2a are integral with each other partly through the integral portion (fused portion) 81. In the portions of the first and second wavy annular members 2a and 2b other than the integral portion (fused portion) 81, the valley of the first wavy annular member 2a and the mountain of the second wavy annular member 2b are connected to each other with a plurality of the short connection portions 4 to form one annular unit. In the embodiment, all the valleys of the first wavy annular member 2a and all the mountains of the second wavy annular member 2b are connected to each other with the connection portions 4 except the integral portion (fused portion) 81. One annular unit has three (less by three than the number of mountains or valleys of annular member) connection portions 4.

The connection portion 4 located in the vicinity of the axial center of the stent 90 is weaker than other constituent parts of the stent 90 and can be broken. As shown in FIGS. 24 and 25, in the stent 90 of the embodiment, the sectional area of each connection portion 4 has a smaller (in other words, narrower) sectional area than that of each of the other parts of the stent 90, namely, the wavy annular members 2a, 2b and the joining portions 181–202. That is, the connection portion 4 is weaker than the other parts of the stent 90. In particular, in the embodiment, the thickness of the connection portion 4 is almost equal to that of the other parts but the width thereof is smaller than that of the other parts.

The annular members 2a, 2b are formed not weakly but the connection portion 4 is formed weakly. A weak portion is not formed on the annular members 2a, 2b. If the weak portion is formed on the annular members 2a, 2b, the annular members 2a, 2b may be naturally broken when the stent 90 is dilated. That is, if the annular members 2a, 2b have the weak portion formed thereon, they may have a low dilating force. But even though the connection portion 4 is formed weakly, the connection portion 4 hardly deforms when the stent 90 is dilated. Thus, the connection portion 4 is hardly broken naturally when the stent 90 is dilated.

Although all the connection portions 4 of the stent 90 are weak, it is possible to form a weak connection portion 4a only in the vicinity of the axial center of the stent 50, as in the case of the stent shown in FIG. 7. The length of the region in which the weak connection portion is formed is preferably 30–60% of the entire length of the stent 50. The region in which the weak connection portion is formed is so formed that the center thereof is located at approximately the center of the stent in the axial direction thereof. In the embodiment shown in FIG. 7, the connection portion 4b located in the vicinity of each axial end of the stent has a width equal to that of the wavy element of each of the annular members 2a, 2b and does not have the weak portion.

Further, instead of making the entire connection portions 4 weak, as in the case of the stent shown in FIGS. 8 through 12, it is possible to form a weak portion on the connection portions 4 such that a portion having a smaller sectional area than the other constituent parts of the stent is formed on the connection portions 4 having the same sectional area as those of the other component parts. As the mode of the weak portion, for example, a nick is formed on each of the opposite side surfaces of the connection portion such that the nicks are axially spaced at a certain interval. As another example, one nick is formed on one side surface of the connection portion such that the nick extends to the widthwise center thereof. As still another example, two nicks are formed on both side surfaces of the connection portion such that the nicks extend to the widthwise center thereof and confront each other. As further example, a portion is formed on the connection portion such that the portion is shorter or thinner than other portions thereof. As still further example, a portion is formed on the connection portion such that the portion is shorter and thinner than other portions thereof.

In the stent 90 of the present invention, an inflating balloon catheter can be inserted into each of the stents such that the inflating balloon catheter penetrates through a side wall of the stent from its interior after the stent is dilated radially. The connection portion can be broken by the inflation of the balloon of the inflating balloon catheter, as shown in FIG. 23. As shown in FIG. 23, each annular member keeps a dilated configuration. Thus the entire stent 90 also keeps a dilated configuration. When the inflating balloon catheter is inserted into the dilated stent and passed the side wall of the stent 90 by guiding with a guide wire and the balloon is inflated, the connection portion of the stent is cut off at the weak portion by the inflated balloon. As a result, a hole having a diameter almost equal to an enlarged diameter of the inflated balloon is formed through the side wall. If the stent does not have the the weak portion, the inflating balloon catheter cannot secure a hole (space) larger than the space formed of a deformation of the annular members to the maximum. Thus, if the balloon is inflated forcibly, it bursts. That is, because the stent has the weak connection portion, the stent is stable in its configuration in a blood vessel.

The joining portions 181–202 joining the wavy annular members of the adjacent annular units 31–42 remain unchanged substantially in their lengths when the stent 90 is dilated. Because the joining portions 181–202 and the connection portion 4 remain substantially unchanged in their lengths even when the stent 90 is dilated, the overall length of the stent 90 remains substantially unchanged before and after dilation. It never happens that the stent is reduced in length after dilation.

The joining portion 181–202 is so disposed that it connects the adjacent annular units 31–42 at two positions. In the embodiment, the joining portion 181–202 may be so disposed that the adjacent ones are continuous with each other.

To reduce the degree of damage to be applied to the inflated balloon when the connection portion 4 is broken, it is preferable that the edge of the wavy element of the stent is chamfered. As the method of chamfering the stent, after the stent is fabricated into a final shape, chemical polishing, electropolishing or mechanical polishing can be used. The chemical polishing is preferably carried out by dipping the stent in a chemical polishing solution for stainless steel. Any chemical polishing solution containing one capable of dissolving stainless steel may be used. For example, one preferable chemical polishing solution contains a mixture of hydrochloric acid and nitric acid serving as a base component and additives such as an organic sulfur compound for adjusting a dissolution rate, smoothing, and imparting luster and a surface active agent.

It is possible that the wavy element of the annular members 2a, 2b located at the opposed ends of the stent 90 in the axial direction thereof has a sectional area, respectively smaller than that of the other wavy annular members. This construction causes the dilation force of the wavy annular members located at the opposed ends of the stent 90 in the axial direction thereof to be lower than those of the other wavy annular members when the stent 90 dilates, but allows the annular members 2a, 2b located at the opposed ends of the stent 90 in the axial direction thereof to follow the bending of a blood vessel to a high extent. That is, the opposed ends of the stent 90 in the axial direction thereof have a high degree of affinity for the blood vessel. As the method of reducing the thickness of the annular members 2a, 2b located at the opposed ends of the stent 90 in the axial direction thereof, after the stent is fabricated into the final shape, the annular members 2a, 2b is chemically polished or mechanically polished.

It is possible that the material of the annular unit (annular member) located at the axial center of the stent 90 have the maximum cross-sectional area and that the annular units (annular member) located nearer to the axial end of the stent have a smaller cross-sectional area than the annular units located nearer to the center of the stent. Specifically, the thickness of the annular units are so set that the thickness of the annular units 34, 35, 36, 37 and 38 located at the axial central part of the stent 90 have a largest thickness and the other annular units have small thicknesses decreasingly as they are nearer to both axial ends of the stent. This construction ensures that the stent 90 displays a sufficient dilating force at its central part and faithfully follows a bent portion of a blood vessel. That is, both axial ends of stent 90 have better affinity for the blood vessel. It is also possible that the annular unit located at the center of the stent 90 has a maximum width and the other annular units have small widths decreasingly as they are nearer to both axial ends of the stent.

In the stent 90, a part of the wavy annular member 2a of one annular unit is in penetration into the wavy space formed at the axial end (inner side of stent) of the other annular unit adjacent to the one annular unit. That is, a part of the mountain of the wavy annular member 2a of one annular unit is in penetration into the concave portion of the wavy annular member 2b formed in the vicinity of the connection portion of the other annular unit adjacent to the one annular unit. Therefore, the adjacent annular units overlap partially each other when the stent 90 is viewed in the axial direction thereof. Thus, when the constituent elements of the wavy annular members are reduced in their lengths in the axial direction of the stent upon dilation of the stent, gaps on the side surface of the stent increase to a small extent. Therefore, it is possible to dilate a stenosed portion of a blood vessel securely and holds an affected portion without a gap.

The mountain of the annular member 2b having one of the joining portions 181–202 formed therein is wider than the other mountains thereof, such that a part of the mountain is adjacent to the joining portion. Similarly, the valley of the annular member 2a having one of the joining portions 181–202 formed therein is wider than the other valleys thereof, such that a part of the valley is adjacent to the joining portion. In the embodiment, the joining portion is approximately linear.

It is preferable that the material of the stent 90 has a certain degree of compatibility with an organism. For example, it is possible to use stainless steel, tantalum or tantalum alloys, platinum or platinum alloys, gold or gold alloys, cobalt base alloys and the like. It is preferable to plate the stent with a noble metal such as gold and platinum after the stent is fabricated into a final shape. As the stainless steel, SUS 316L most corrosion-resistant of the above metals can be preferably used.

It is preferable to anneal the stent 90 after it is fabricated into the final shape. Annealing improves the flexibility and plasticity of the entire stent so that the stent can be effectively implanted in a curved blood vessel. As compared with a non-annealed stent, the annealed stent has a lower force of restoring to an original state after it is dilated, and especially has a lower force of restoring to an original linear state when it is dilated at a curved portion of a blood vessel. This minimizes physical stimulation to the inner wall of the curved blood vessel, thus reducing the cause of a recurrence of stenosis. The stent is preferably annealed by heating it to 900 to 1200° C. in an inert gas atmosphere (e.g., a mixture gas of nitrogen and hydrogen) so that no oxide film is formed on the surface of the stent and then slowly cooling it.

The stent 1 has a diameter favorably 0.8 to 1.8 mm and more favorably 1.0 to 1.6 mm in an undilated state. The stent 90 has a length favorably 9 to 40 mm in an undilated state. The length of each of the wavy annular members 2a, 2b has a length of 0.7 to 2.0 mm. The length of one of the annular units 31 through 42 is favorably 1.5–4.0 mm and more favorably 2.0–3.0 mm. The length of one connection portion 4 is favorably 0.01–0.5 mm. The number of the annular units 31 through 42 is 3 to 50. The constituent elements (annular member) of the adjacent annular units have an axial overlap of about 0.5 to 1 mm. The distance between the center of one annular units and that of the annular unit adjacent thereto is preferably 1.3 to 2.5 mm. The length of each of the joining portions 181–202 is preferably 1.4 to 2.7 mm. The angle of inclination (the angle of inclination of the joining portion relative to a longitudinal direction in a development view) of each of the joining portion 181 through 202 relative to the axis of the stent is favorably 0° to 30° and more favorably 5° to 25°.

The thickness of each of the wavy annular members 2a, 2b (wavy elements, wavy line-shaped elements) of the stent 90 and that of each of the joining portions 181–202 are favorably 0.05 to 0.15 mm and more favorably 0.08 to 0.12 mm. The width of each of the wavy annular members 2a, 2b and that of each of the joining portions 181–202 are favorably 0.07 to 0.15 mm and more favorably 0.08 to 0.12 mm. The thickness of the connection portion 4 of the stent 90 is favorably 0.05–0.12 mm and more favorably 0.06–0.10 mm. The width of the connection portion 4 of the stent 90 is favorably 0.01–0.05 mm and more favorably 0.02 to 0.04 mm. The sectional area of the connection portion 4 is favorably 1/50 to 1/2 of that of the other parts (annular member and joining portion) and more favorably 1/20 to 1/10 of that of the other parts.

An embodiment of the blood vessel dilation device of the present invention is described below with reference to the drawings.

Figure 14:
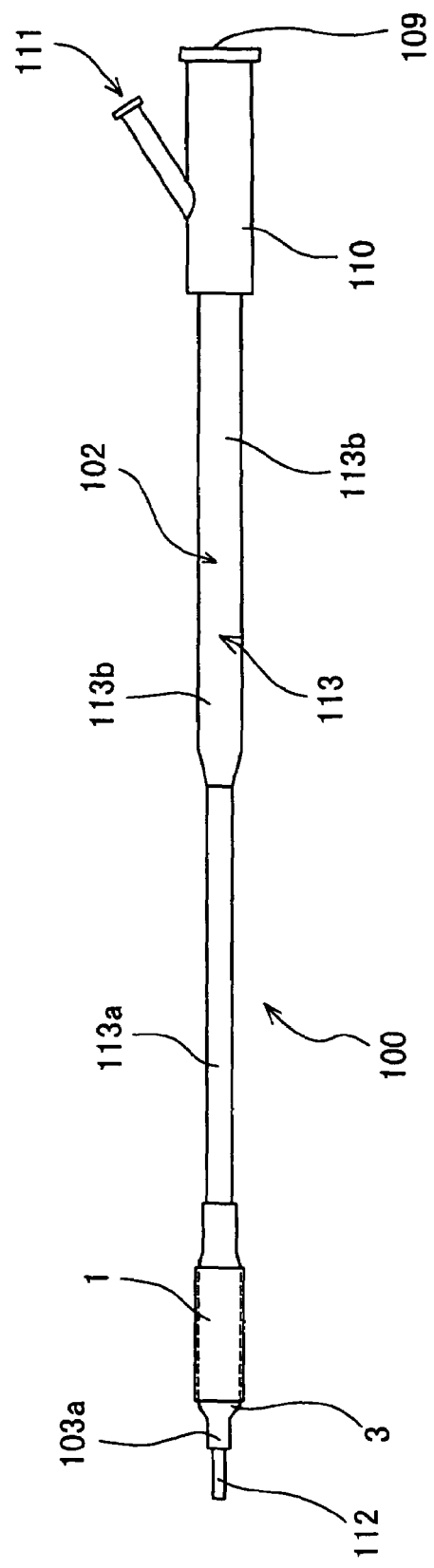
FIG. 14 is a front view of a organ dilation device according to an embodiment of the present invention.
Figure 15:
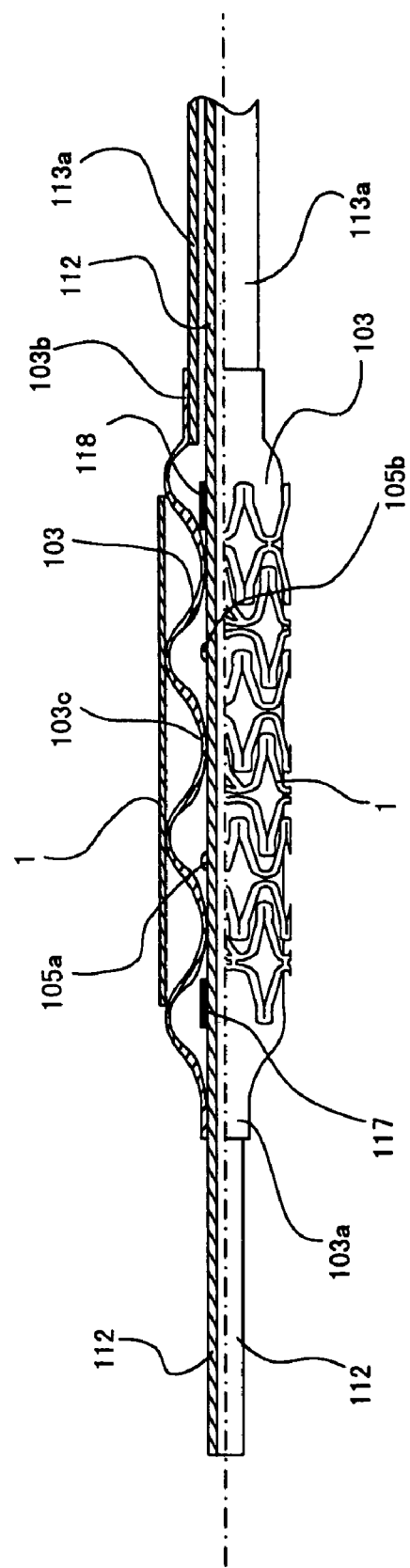
FIG. 15 is a partly enlarged sectional view showing a front end of the organ dilation device shown in FIG. 14.
Figure 16:
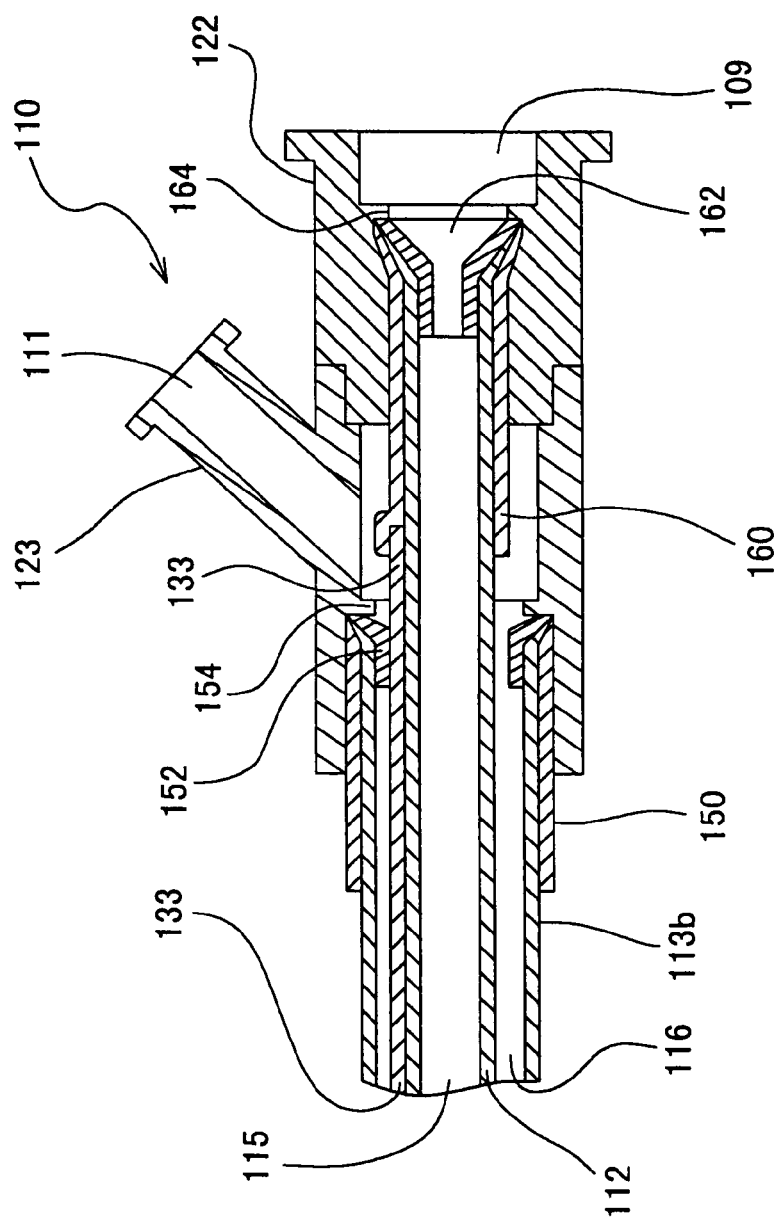
FIG. 16 is an enlarged sectional view showing a rear end of the organ dilation device shown in FIG. 14.
Figure 17:
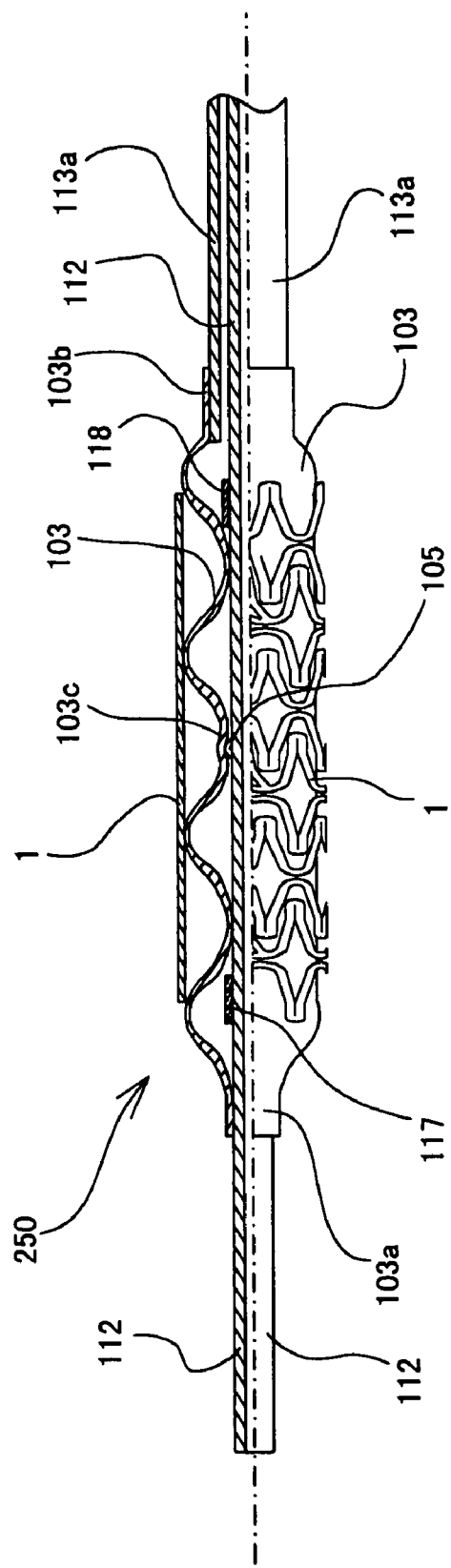
FIG. 17 is a partly enlarged sectional view showing a front end of a organ dilation device according to another embodiment of the present invention.

FIG. 14 is a front view of a organ dilation device according to an embodiment of the present invention. FIG. 15 is a partly enlarged sectional view showing a front end of the organ dilation device shown in FIG. 14. FIG. 16 is a partly enlarged sectional view showing a rear end of the organ dilation device shown in FIG. 14. FIG. 17 is a partly enlarged sectional view showing a front end of a organ dilation device according to another embodiment of the present invention.

A blood vessel dilation device 100 of the present invention has a tubular shaft body 102, a foldable and expandable balloon 103 provided on a front end of the shaft body 102; and a stent 1 installed on the folded balloon 103 so that the stent 1 covers the balloon 103 and dilated by expansion of the balloon 103.

The stent 1 is formed in a substantially tubular configuration and has a diameter so set that it is inserted into the body. The stent 1 can be dilated when a force acting radially outwardly is applied thereto from the interior thereof. The stent 1 has a plurality of wavy annular members consisting of the wavy element and arranged in the axial direction of the stent 1 and a plurality of connection portions each connecting the adjacent wavy annular members to each other axially. The connection portion located in the vicinity of the axial center of the stent 1 is weaker than the other constituent parts thereof and can be broken.

The shaft body 102 of the blood vessel dilation device 100 of the present invention has a balloon expansion lumen communicating with the inside of the balloon 103. The blood vessel dilation device 100 has a radiographing member 105 fixed to an outer surface of the shaft body 102 such that the fixing position of the radiographing member 105 is located at the center of the stent 1 or radiographing members 105a, 105b fixed to the outer surface of the shaft body 102 (in the embodiment, inner tube 112) such that the fixing positions of the radiographing members 105a, 105b are located at one and other ends of the central region, of the stent 1, having a predetermined length.

In the organ dilation device 100 of the embodiment, as shown in FIG. 14, the shaft body 102 has a guide wire lumen 115 whose one end is open at a front end of the shaft body 102 and other end is open at a rear end thereof.

The organ dilation device 100 of the present invention has the tubular shaft body 102, the stent-dilating balloon 103 attached to the front end of the shaft body 102; and the stent 1 installed on the balloon 103. The shaft body 102 has an inner tube 112, an outer tube 113, and a branch hub 110.

As shown in FIGS. 15 and 16, the inner tube 112 has a guide wire lumen 115 for inserting a guide wire thereinto. The length of the inner tube 112 is favorably 100 to 2000 mm and more favorably 150–1500 mm. The outer diameter of the inner tube 112 is favorably 0.1 to 1.0 mm and more favorably 0.3 to 0.7 mm. The thickness of the inner tube 112 is favorably 10 to 150 µm and more favorably 20 to 100 µm. The inner tube 112 is inserted into the outer tube 113 to such an extent that the front end of the inner tube 112 projects from the outer tube 113. A balloon expansion lumen 116 is formed between the outer surface of the inner tube 112 and the inner surface of the outer tube 113 and has a large volume. The front end of the outer tube 113 into which the inner tube 112 is inserted is located a little rearward from the front end of the inner tube 112.

The length of the outer tube 113 is favorably 100 to 2000 mm and more favorably 150–1500 mm. The outer diameter of the outer tube 113 is favorably 0.5 to 1.5 mm and more favorably 0.7 to 1.1 mm. The thickness of the outer tube 113 is favorably 25 to 200 µm and more favorably 50 to 100 µm.

In the organ dilation device 100 of the embodiment, the outer tube 113 consists of a front-end side outer tube 113a and a shaft body side outer tube 113b joined with the front-end side outer tube 113a. The diameter of the front-end side outer tube 113a decreases in the region from the joining position at which the front-end side outer tube 113a and the shaft body side outer tube 113b are joined with each other to a position spaced at a certain interval forward from the joining position. Therefore, in the tapered region, the diameter of the front-end side outer tube 113a decreases gradually. The diameter thereof except the tapered region is constant and smaller than that of the front end of the tapered region.

The outer diameter of the front-end side outer tube 113a at its smaller-diameter portion is favorably 0.50 to 1.5 mm and more favorably 0.60 to 1.1 mm. The outer diameter of the front-end side outer tube 113a at its rear end portion and that of the shaft body side outer tube 113b are favorably 0.75 to 1.5 mm and more favorably 0.9 to 1.1 mm.

The balloon 103 has a front-end side bonding portion 103a and a rear-end side bonding portion 103b. The front-end side bonding portion 103a is fixed to the inner tube 112 at a position a little rearward from the front end thereof. The rear-end side bonding portion 103b is fixed to the front end of the outer tube 113. The balloon 103 communicates with the balloon expansion lumen 116 at a position in the vicinity of the rear end of the balloon 103.

A material having a certain degree of flexibility can be preferably used for the inner tube 112 and the outer tube 113. It is favorable to use thermoplastic resins such as polyolefin (for example, polyethylene, polypropylene, ethylene-propylene copolymer, ethylene-vinyl acetate copolymer), polyvinyl chloride, polyamide elastomer, and polyurethane; silicone rubber; latex rubber; and the like. It is more favorable to use the thermoplastic resins. Polyolefin is the most favorable of the thermoplastic resins.

As shown in FIG. 15, the balloon 103 is foldable. When the balloon 103 is not expanded, it can be folded over the outer surface of the inner tube 112. The balloon 103 has a tubular (preferably, cylindrical) expandable portion having an approximately uniform diameter so that the stent 1 to be installed on the balloon 103 can be dilated. The expandable portion is not necessarily cylindrical but may be polygonal. As described above, the front-end side bonding portion 103a of the balloon 103 is liquid-tightly bonded to the inner tube 112, and the rear-end side bonding portion 103b thereof is liquid-tightly bonded to the front end of the outer tube 113 with an adhesive agent or thermal fusion. The balloon 103 tapers between the expandable portion and each of the bonding portions 103a and 103b.

An expansion space 103c is formed between the inner surface of the balloon 103 and the outer surface of the inner tube 112. The entire circumference of the expansion space 103c communicates with the balloon expansion lumen 116 at the rear end of the expansion space 103c. Because the expansion space 103c communicates with the balloon expansion lumen 116 having a comparatively large volume, it is easy to inject an expansion fluid into the balloon 103 through the balloon expansion lumen 116.

A material having a certain degree of flexibility can be preferably used for the balloon 103. It is favorable to use thermoplastic resins such as polyolefin (for example, polyethylene, polypropylene, ethylene-propylene copolymer, ethylene-vinyl acetate copolymer, cross link type of ethylene-vinyl acetate copolymer, polyvinyl chloride, polyamide elastomer, and polyurethane, polyester (for example, polyethylene terephthalate), polyarylane sulfide (for example, polyphenylene sulfide); silicone rubber; latex rubber and the like. It is particularly favorable to use extensible material. A biaxially oriented material can be preferably used for the balloon 103 because of its high degree of strength and expansion.

Regarding the size of the balloon 103, the outer diameter of the dilated cylindrical portion (expandable portion) thereof is favorably 2 to 4 mm and more favorably 2.5 to 3.5 mm. The length of the balloon 103 is favorably 10 to 50 mm and more favorably 20 to 40 mm. The outer diameter of the front-end side bonding portion 103a is favorably 0.9 to 1.5 mm and more favorably 1 to 1.3 mm. The length of the front-end side bonding portion 103a is favorably 1 to 5 mm and more favorably 1 to 1.3 mm. The outer diameter of the rear-end side bonding portion 103b is favorably 1 to 1.6 mm and more favorably 1.1 to 1.5 mm. The length of the rear-end side bonding portion 103b is favorably 1 to 5 mm and more favorably 2 to 4 mm.

As shown in FIG. 15, the blood vessel dilation device 100 has radiographing members 105a, 105b fixed to the outer surface of the shaft body 102 (in the embodiment, inner tube 112) such that the fixing positions of the radiographing members 105a, 105b are located at one and other ends of the central region, of the stent 1, having a predetermined length. Therefore, in introducing the stent 1 into a branched blood vessel, it is easy to implant the stent 1 such that the central region thereof is disposed at the branch portion. The distance between the radiographing members 105a and 105b is preferably 2–5 mm and favorably 10–70% of the entire length of the stent 1 and more favorably 10–50% of the entire length thereof.

As shown in FIG. 17 showing another embodiment, the blood vessel dilation device 250 may have a radiographing member 105 fixed to the outer surface of the shaft body such that the installing position of the radiographing member 105 is located at the center of the stent 1. The blood vessel dilation device 100 has two radiographing members 117, 118 fixed to the outer surface of the shaft body 102 such that the radiographing member 117, 118 are located at one and other ends of the cylindrical portion (expandable portion) of the balloon 103 when the stent is dilated.

The radiographing members 105, 105a, 105b, 117, and 118 are preferably in the shape of a ring having a predetermined length, a coiled wire or the like. It is preferable that the radiographing members 105, 105a, 105b, 117, and 118 are made of gold, platinum, tungsten or alloys thereof or a silver-palladium alloy or the like.

As the stent 1 for use in the organ dilation devices 100 and 250 of the present invention, all of the above-described stents can be used.

As shown in FIG. 16, a linear reinforcement member 133 is inserted between the inner tube 112 and the outer tube 113, namely, into the balloon expansion lumen 116. The reinforcement member 133 prevents excess bending of the body of the organ dilation device 100 at bent portions of blood vessels without much deteriorating the flexibility of the organ dilation device 100 and facilitates the insertion of the frond end of the organ dilation device 100 into the bent portions of blood vessels. The diameter of the frond end of the reinforcement member 133 is set smaller than those of the other portions thereof by grinding or the like. It is preferable that front end of the small-diameter extends to the vicinity of the front end of the outer tube 113 of the body of the organ dilation device 100. It is preferable that the reinforcement member 133 consists of a metal wire having a diameter 0.05 to 1.50 mm and more favorably 0.10 to 1.00 mm. The reinforcement member 133 is made of favorably an elastic metal such as stainless steel or a super elastic alloy and more favorably high-strength stainless steel for a spring or a super elastic alloy.

As shown in FIG. 16, the organ dilation device 100 of the embodiment has a branched hub 110 fixed to the rear end thereof.

The branched hub 110 consists of an inner-tube hub 122 fixed to the inner tube 112 and having a guide wire introducing opening 109 communicating with the guide wire lumen 115 and forming a guide wire port; and an outer-tube hub 123 fixed to the outer tube 113 and having an injection port 111 communicating with the balloon expansion lumen 116. The outer-tube hub 123 and the inner-tube hub 122 are fixed to each other. As the material of the branched hub 110, thermoplastic resin such as polycarbonate, polyamide, polysulfone, polyacrylate and methacrylate-butylene-stylene copolymer can be preferably used.

In the embodiment, the outer tube 113 has a bending-preventing tube 150 mounted on the rear end portion thereof. The bending-preventing tube 150 is formed of a heat-shrinkable material so that its inner diameter becomes a little smaller than the outer diameter of the outer tube 113 after the bending-preventing tube 150 shrinks with heat. The bending-preventing tube 150 thus formed is installed on the rear end portion of the outer tube 113 by fitting the bending-preventing tube 150 on the rear end portion of the outer tube 113 and heating (for example, with hot air) the bending-preventing tube 150 to shrink it. The bending-preventing tube 150 is fixed to the outer-tube hub 123 with a retaining pin 152. The outer diameter of the cylindrical retaining pin 152 is approximately equal to the inner diameter of the outer tube 113 except the rear end portion thereof. That is, the outer diameter of the cylindrical retaining pin 152 at its rear end portion is larger than the outer diameter at the other portion thereof. Describing the method of installing the bending-preventing tube 150 on the outer-tube hub 123 in detail, the retaining pin 152 is inserted into the rear end of the outer tube 113. Then, the outer tube 113 is inserted into the outer-tube hub 123, with the front end thereof leading and pressed until the rear end of the retaining pin 152 passes a projection 154 formed on the inner surface of the outer-tube hub 123. An adhesive agent may be applied to the contact surface of the outer-tube hub 123 and that of the bending-preventing tube 150 to secure the bending-preventing tube 150 to the outer-tube hub 123.

The inner tube 112 has a bending-preventing tube 160 mounted on the rear end portion thereof. The bending-preventing tube 160 is formed of a heat-shrinkable material so that its inner diameter becomes a little smaller than the outer diameter of the inner tube 112 after the bending-preventing tube 160 shrinks with heat. The bending-preventing tube 160 thus formed can be easily installed on the rear end portion of the inner tube 112 by fitting the bending-preventing tube 160 on the rear end portion of the inner tube 112 and heating (for example, with hot air) the bending-preventing tube 160 to shrink it. The rear end of the reinforcement member 133 is fixed to the outer surface of the inner tube 112 with the bending-preventing tube 160. The inner tube 112 on which the bending-preventing tube 160 has been installed is fixed to the inner-tube hub 122. The bending-preventing tube 160 is fixed to the inner tube 112 with a retaining pin 162. The outer diameter of the cylindrical retaining pin 162 is approximately equal to the inner diameter of the inner tube 112 except the rear end portion thereof. That is, the outer diameter of the cylindrical retaining pin 162 at its rear end portion is larger than the outer diameter at the other portion thereof. Describing the method of installing the bending-preventing tube 160 on the inner-tube hub 122 in detail, the retaining pin 162 is inserted into the rear end of the inner tube 112. Then, the inner tube 112 is inserted into the inner-tube hub 122, with the front end thereof leading and pressed until the rear end of the retaining pin 162 passes a projection 164 formed on the inner surface of the inner-tube hub 122. An adhesive agent may be applied to the contact surface of the inner-tube hub 122 and that of the bending-preventing tube 160 to secure the inner tube 112 to the inner-tube hub 122.

As the material of the outer-tube hub and the inner-tube hub, thermoplastic resin such as polycarbonate, polyamide, polysulfone, polyacrylate, and methacrylate-butylene-styrene copolymer can be preferably used.

The inner-tube hub 122 and the outer-tube hub 123 are fixed to each other by inserting the inner tube 112 into the rear end of the outer-tube hub 123 installed on the rear end of the outer tube 113, with the front end of the inner tube 112 leading. The inner-tube hub 122 and the outer-tube hub 123 can be securely fixed to each other by applying an adhesive agent to the joining portion of each thereof.

The construction of the rear end portion of the organ dilation device 100 is not limited to the above-described one. For example, instead of the branched hub 110, a tube having a port member forming an opening at its rear end may be liquid-tightly installed on the guide wire lumen 115 and the balloon expansion lumen 116, respectively.

Figure 18:
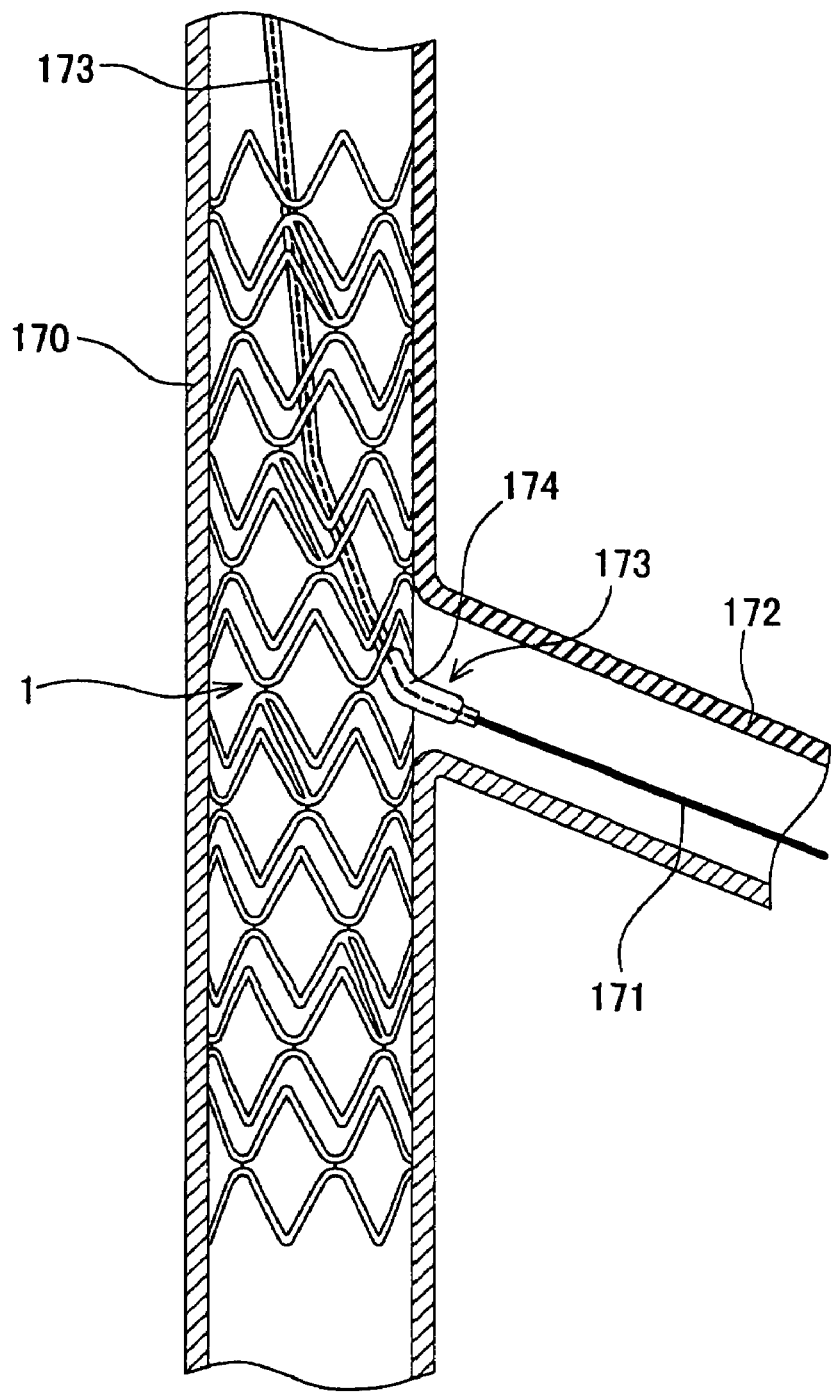
FIG. 18 is an explanatory view for describing the operation of the stent of the present invention.

The method of using the stent of the present invention and the blood vessel dilation device of the present invention will be described below. FIGS. 18 and 19 are explanatory views for describing the operation of the stent of the present invention and that of the blood vessel dilation device thereof.

The blood vessel dilation device 100 has the stent 1 and the balloon catheter for dilating the stent 1 in a blood vessel. The blood vessel dilation device 100 is inserted into a sheath, and a guide wire is introduced into the blood vessel dilation device. Then, under the guide of the guide wire, the blood vessel dilation device is introduced into a stenosed portion of a branched blood vessel. After the guide wire passes through the stenosed portion of the branched blood vessel, the blood vessel dilation device is progressed along the guide wire. After the blood vessel dilation device and the sheath are introduced into the stenosed portion, using a fluoroscope, the blood vessel dilation device is located in the stenosed portion such that the two radiographing members indicating the central portion of the stent straddles the branch portion. Then, the sheath is moved rearward. Then, a contrast medium is injected into the balloon under a high pressure to inflate the balloon. As a result of the inflation of the balloon, the stent 1 undergoes a plastic deformation, i.e., it dilates (inflates) radially outwardly, thus widening the stenosed portion. Then, the pressure of the balloon is removed to contract it. The stent does not contract owing to its plastic deformation caused dilation state-keeping force (configuration-keeping force) and thus stays at the stenosed portion, thereby keeping the blood vessel dilated and improving blood stream disorder.

To secure a favorable blood stream to the branched blood vessel and implant the stent therein, an operation of partly breaking a side wall of the stent positioned at an opened portion of the branch portion of the blood vessel is performed. In the operation of breaking the side wall of the stent partly, as shown in FIG. 18, initially, a guide wire 171 is introduced into a main blood vessel 170. Then, the front end of the guide wire 171 is penetrated through the side wall of the stent 1 to insert the guide wire 171 into branched blood vessel 172. Then, using the guide wire 171, an dilating balloon catheter 173 (having an outer diameter allowing the catheter 173) for use in the blood vessel dilation device and penetrable through the side wall of the stent is so guided that the front end of the catheter 173 reaches the interior of the branched blood vessel 172 and that the central portion of a balloon 174 of the catheter 173 crosses the side wall of the stent 1. This state is shown in FIG. 18.

Then, the balloon is inflated to break the connection portion 4 that is the weak portion of the stent 1, as shown in FIG. 19. As a result, an enlarged opening 177 larger than other portions of the stent 1 is formed on the side wall of the stent 1. The enlarged opening 177 reduces the possibility that blood flowing from the main blood vessel 170 to the branched blood vessel 172 is blocked and allows insertion of another balloon catheters, blood vessel dilation device, and stent into the branched blood vessel 172.

EXAMPLE

Example 1

A metal pipe used in example 1 was made of stainless steel (SUS 316L) having a diameter of 1.4 mm, a thickness of 0.10 mm, and a length of 100 mm.

A stent was prepared by hollowing out a metal pipe to leave a stent skeleton. A stent skeleton can be hollowed out of a metal pipe in many ways. Exemplary processes include an etching process, known as photo-fabrication, using masks and chemicals, electric discharge machining, and mechanical machining. A laser machining processing method was used herein because it is simplest to operate and highest in precision.

A laser machining device used was a YAG laser model SL116E manufactured by NEC. The metal pipe was mounted on a jig equipped with a rotating motor and a fastening mechanism to prevent run-out of the metal pipe. The jig was set on a numerically controllable XY table. The XY table and the rotating motor were connected to a personal computer such that an output of the personal computer was transmitted to a numerical controller of the XY table and the rotating motor. A development drawing representing the stent having the structure shown in FIG. 2 was inputted to the personal computer storing a design software.

The XY table and the rotating motor were driven in accordance with design data outputted from the personal computer. The pipe was irradiated with a laser beam to machine the pipe into a stent structure having the configuration shown in FIG. 1.

A mandrel was inserted into the pipe to prevent the laser beam from penetrating throughout the pipe. As the laser machining condition for the metal pipe, current value was 25 A, an output was 1.5 W, and a drive speed was 10 mm/min. The machine is not limited to the above-described system but it is possible to use a laser marker of the galvanometer system to be driven by a laser machining device.

A stent structure having the configuration shown in FIGS. 1 through 3 was prepared in this manner. The stent structure was dipped in a stainless steel chemical polishing solution at about 98° C. for about 10 minutes to chamfer (deburr and chemically polish) the stent structure. The chemical polishing solution used in example 1 was a solution containing a mixture of hydrochloric acid and nitric acid serving as a main component, an organic sulfur compound, and a surface active agent. The chemical polishing solution is commercially available as Sunbit 505 from Sanshin Chemical Industry K.K.

In this manner, the stent of the present invention having the configuration shown in FIGS. 1 through 3 was prepared. The stent had an entire length of 20 mm and an outer diameter of 1.4 mm. The width of a portion constituting a wavy element (wavy annular member) and a joining portion was 0.12 mm. A connection portion had a width of 0.03 mm and a length of 0.1 mm. All the stent had a thickness of about 0.08 mm.

Example 2

Similarly to example 1, a metal pipe made of stainless steel (SUS 316L) having a diameter of 1.4 mm, a thickness of 0.10 mm, and a length of 100 mm.

Using a method similar to that of example 1, a development drawing representing a stent having the construction shown in FIG. 5 was inputted to the design software of the personal computer.

The stent of the present invention having the configuration shown in FIGS. 4 through 7 was prepared. Similarly to example 1, the stent was chamfered. The stent had an entire length of 20 mm and an outer diameter of 1.4 mm. The width of a portion constituting the wavy element (wavy annular member) and the connection portion was 0.12 mm, respectively. The narrowest portion of the slit-formed portion (weak portion) of the connection portion had a width of 0.02 mm. The connection portion had a length of 3 mm. All the stent had a thickness of about 0.08 mm.

Comparison Example 1

Using a method similar to that of example 1, a stent having the same configuration as that shown in FIGS. 1 through 3 was prepared, but the connection portion was different from that shown in FIGS. 1 through 3. The stent had an entire length of 20 mm and an outer diameter of 1.4 mm. The width of a portion constituting the wavy element (wavy annular member), the joining portion, and the connection portion was 0.12 mm, respectively. The connection portion had a length of 0.1 mm. All the stent had a thickness of about 0.08 mm.

Comparison Example 2

Using a method similar to that of example 2, a stent having the same configuration as that shown in FIGS. 4 through 7 was prepared, but the weak portion was not formed on the connection portion. The stent had an entire length of 20 mm and an outer diameter of 1.4 mm. The width of a portion constituting the wavy element (wavy annular member) and the connection portion was 0.12 mm, respectively. The connection portion had a length of 3 mm. The stent had a thickness of about 0.08 mm.

Experiment 1

The stent of each of examples 1 and 2 and comparison examples 1 and 2 was mounted on a balloon of an expandable catheter (balloon catheter) for PTCA. Each stent was dilated to have a diameter of 3 mm. As a result, the stent of example 1 and that of comparison example 1 deformed as shown in FIG. 4, and the stent of example 2 and that of comparison example 2 deformed as shown in FIG. 11. The connection portion of each stent was not broken.

Experiment 2

The expandable catheter (balloon catheter) for PTCA having an expanded diameter of 3 mm was inserted into the stent of each of examples 1 and 2 and comparison examples 1 and 2 from the lumen thereof such that the catheter penetrated through the side wall of the stent and the front end thereof projected to the outside. After the balloon crossed the side wall of the stent, the balloon was expanded. The result was that in the stent of each of examples 1 and 2, one connection portion was broken and the balloon could be expanded to a length of 3 mm. At the cutting point of the stent of example 1, the thickness was about 0.08 mm, the width was 0.03 mm, the sectional area was 0.0024 mm$^2$. At the cutting point of the stent of example 2, the thickness was about 0.09 mm, the width was 0.02 mm, the sectional area was 0.0016 mm$^2$. The stent of each of comparison examples 1 and 2 burst when the pressure of the balloon became about 16 atm when the balloon was inflated.

Example 3

Similarly to example 1, a metal pipe made of stainless steel (SUS 316L) having a diameter of 1.4 mm, a thickness of 0.1 mm, and a length of 100 mm.

Using a method similar to that of example 1, a development drawing representing a stent having the construction shown in FIG. 21 was inputted to the design software of the personal computer.

The stent of the present invention having the configuration shown in FIG. 20 was prepared. Similarly to example 1, the stent was chamfered. The stent had an entire length of 20 mm and an outer diameter of 1.4 mm. The width of a portion constituting the wavy element (wavy annular member) and the connection portion was 0.12 mm. The integral portion had a width of 0.20 mm. The connection portion had a width of 0.03 mm and a length of 0.05 mm. All the stent had a thickness of about 0.08 mm.

Example 4

Similarly to example 1, a metal pipe made of stainless steel (SUS 316L) having a diameter of 1.4 mm, a thickness of 0.1 mm, and a length of 100 mm.

Using a method similar to that of example 1, a development drawing representing a stent having the construction shown in FIG. 25 was inputted to the design software of the personal computer.

The stent of the present invention having the configuration shown in FIG. 24 was prepared. Similarly to example 1, the stent was chamfered. The stent had an entire length of 20 mm and an outer diameter of 1.4 mm. The width of a portion constituting the wavy element (wavy annular member) and the connection portion was 0.12 mm. The integral portion had a width of 0.20 mm. The connection portion had a width of 0.03 mm and a length of 0.05 mm. All the stent had a thickness of about 0.08 mm.

Comparison Example 3

Using a method similar to that of example 1, a stent having the same configuration as that shown in FIG. 20 was prepared, but the connection portion was different from that shown in FIGS. 1 through 3. The stent had an entire length of 20 mm and an outer diameter of 1.4 mm. The width of a portion constituting the wavy element (wavy annular member), the joining portion, and the connection portion was 0.12 mm, respectively. The integral portion had a width of 0.20 mm. The connection portion had a width of 0.10 mm and a length of 0.05 mm. All the stent had a thickness of about 0.08 mm.

Comparison Example 4

Using a method similar to that of example 1, a stent having the same configuration as that shown in FIG. 24 was prepared, but the connection portion was different from that shown in FIGS. 1 through 3. The stent had an entire length of 20 mm and an outer diameter of 1.4 mm. The width of a portion constituting the wavy element (wavy annular member), the joining portion, and the connection portion was 0.12 mm, respectively. The integral portion had a width of 0.20 mm. The connection portion had a width of 0.10 and a length of 0.05 mm. All the stent had a thickness of about 0.08 mm.

Experiment 3

The stent of each of examples 3 and 4 and comparison examples 3 and 4 was mounted on a balloon of an expandable catheter (balloon catheter) for PTCA. Each stent was dilated to have a diameter of 3 mm. As a result, the diameter of the stent of example 3 and 4 and that of comparison example 3 and 4 dilated. The connection portion of each stent was not broken.

Experiment 4

The expandable catheter (balloon catheter) for PTCA having a diameter of 3 mm in an inflated state was inserted into the stent of example 3 and 4 and that of comparison example 3 and 4 from the lumen thereof such that the catheter penetrated through the side wall of the stent and the front end thereof projected to the outside. After the balloon crossed the side wall of the stent, the balloon was expanded. The result was that in the stent of example 3, one connection portion was broken and the balloon could be so inflated that it had an increased diameter of 3 mm. The cutting point of the stent of example 3 had a thickness of about 0.08 mm, a width of 0.03 mm, and a sectional area of 0.0024 $mm^2$. The cutting point of the stent of example 4 had a thickness of about 0.08 mm, a width of 0.03 mm, and a sectional area of 0.0024 $mm^2$. On the other hand, the stent of comparison examples 3 burst when the pressure of the balloon became about 16 atm when the balloon was inflated. The stent of comparison examples 4 burst when the pressure of the balloon became about 16 atm when the balloon was inflated.

The stent of the present invention is formed in a substantially tubular configuration and has a diameter so set that the stent is inserted into the body. The stent can be dilated radially outwardly upon application of a force acting radially outwardly from the interior of the tubular stent. The stent has a plurality of wavy annular members each formed of a narrow wavy element and arranged in the axial direction thereof; and a plurality of connection portions each connecting the adjacent wavy annular members to each other axially. The connection portion located in the vicinity of the axial center of the stent is weaker than the other constituent parts of the stent and can be broken. Owing to the construction, an inflating balloon catheter can be inserted into the stent such that the inflating balloon catheter penetrates through a side wall of the stent from its interior after the stent is dilated radially. The connection portion can be broken by the inflation of the balloon of the inflating balloon catheter.

In this construction, when the stent embedded in a visinity of a branch portion of a blood vessel, the connection portion of the stent can be partly broken, using the balloon catheter or the like. Consequently, it is possible to form an enlarged opening on the side wall of the stent located at an opened portion formed at the inlet of the branched blood vessel. The enlarged opening reduces the possibility that blood flowing from a main blood vessel to the branched blood vessel is blocked and prevents thrombus from arising at the branched portion. Further, using the enlarged opening formed on the side wall of the stent, it is possible to insert another balloon catheter, blood vessel dilation device and stent into the branched blood vessel.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A stent that is to be implanted in a body formed in a substantially tubular configuration, has a diameter so set that the stent is insertable into the body, and can be dilated radially outwardly upon application of a force acting radially outwardly from the interior thereof, the stent having a plurality of wavy annular members each formed of a wavy element and arranged in the axial direction thereof;

and a plurality of connection portions each connecting the adjacent wavy annular members to each other axially;

wherein at least some of the connection portions are breakable connection portions that are configured to be weaker than other parts of the stent so as to be broken by inserting an inflating balloon catheter into the stent after the stent is radially dilated and through a side of the stent from an interior of the stent and inflating the inflating balloon catheter;

the stent comprising a plurality of annular units arranged in the axial direction of the stent and joining portions each connecting the annular units to each other;

wherein each annular unit comprises a first wavy annular member formed of a wavy element; a second wavy annular member disposed in the axial direction of the stent such that a mountain of the second wavy annular member is proximate to a valley of the first wavy annular member and formed of a wavy element; an integral portion consisting of the valley of the first wavy annular member and the mountain of the second wavy annular member integrated therewith; and a plurality of the connection portions each connecting the valley of the first wavy annular member and the mountain of the second wavy annular member to each other;

the connection portions being located in a vicinity of the center of the stent;

the joining portions connecting adjacent annular units to each other through the integral portions;

the joining portions being so arranged that those adjacent to each other are continuous with each other and more than two of the joining portions are not continuous with each other;

the stent having joining portions-continuous members consisting of the continuous joining portion, connecting three annular units to each other at the integral portions thereof and bending at its center; and the joining portions-continuous members are dislocated from each other by a length of one joining portion in a rear-end direction of the stent.

2. A stent according to claim 1, wherein the connection portions located in the vicinity of the center of the stent in the axial direction there have a breakable weak portion.

3. A stent according to claim 1, wherein an entirety of each of the connection portions located in the vicinity of the center of the stent in the axial direction thereof is formed as a weak portion.

4. A stent according to claim 2, wherein the weak portion has a smaller sectional area than other constituent parts of the stent.

5. A stent according to claim 1, wherein a part of the wavy annular member of one annular unit penetrates into a wavy space formed in another one of the annular units adjacent to the one annular unit.

6. A stent according to claim 1, wherein all the connection portions are weaker than other parts of the stent and can be broken.

7. A stent according to claim 1, wherein the annular units have at least two integral portions.

8. A stent according to claim 7, wherein the integral portions are so formed that they are not adjacent to each other.

9. A stent according to claim 1, wherein adjacent joining portions-continuous members have different bending directions.

10. A dilation device having a tubular shaft body; a foldable and expandable balloon provided to a front-end portion of the shaft body; and a stent installed on the folded balloon and dilating by expansion of the balloon, wherein the stent is the stent of claim 1; the shaft body has a balloon expansion lumen communicating with the inside of the balloon; and the dilation device has a radiographing member fixed to an outer surface of the shaft body such that a fixing position of the radiographing member is located at a center of the stent or has two radiographing members fixed to the outer surface of the shaft body such that the fixing positions of the radiographing members are located at one and other ends of a central region, of the stent, having a predetermined length.

11. A dilation device according to claim 10 wherein the balloon has an expandable portion that is expanded into the shape of a cylinder having an approximately uniform diameter by a fluid injected into the balloon expansion lumen and has two radiographing members fixed to the outer surface of the shaft body such that the fixing positions of the radiographing members are located at one and other ends of the expandable portion.

* * * * *

UNITED STATES PATENT AND TRADEMARK OFFICE
CERTIFICATE OF CORRECTION

PATENT NO. : 7,029,492 B2  Page 1 of 1
APPLICATION NO. : 09/518540
DATED : April 18, 2006
INVENTOR(S) : Kazuaki Mitsudou and Yousuke Moriuchi It is certified that error appears in the above-identified patent and that said Letters Patent is hereby corrected as shown below:

Column 1, line 9, change "dosed" to --closed--.

Column 1, line 12, change "dosed" to --closed--.

Column 1, line 14, change "dosed" to --closed--.

Column 1, line 17, after "make", delete the hyphen.

Column 1, line 18, change "dosed" to --closed--.

Column 1, line 26, change "dose" to --close--.

Column 9, line 47, after "inflating", delete the hyphen.

Column 11, line 16, change "3142" to --31-42--.

Column 16, line 67, change "120'" to --120°--.

Column 17, line 3, change "120'" to --120°--.

Signed and Sealed this

Sixteenth Day of January, 2007

JON W. DUDAS
*Director of the United States Patent and Trademark Office*